US010085633B2

(12) United States Patent
Schaller et al.

(10) Patent No.: US 10,085,633 B2
(45) Date of Patent: Oct. 2, 2018

(54) DIRECT VISUALIZATION SYSTEM FOR GLAUCOMA TREATMENT

(71) Applicant: Novartis AG, Basel (CH)

(72) Inventors: Michael Schaller, Menlo Park, CA (US); Tsontcho Ianchulev, Menlo Park, CA (US); Richard S. Lilly, Menlo Park, CA (US); Luke Clauson, Menlo Park, CA (US); David Lari, Menlo Park, CA (US)

(73) Assignee: Novartis AG, Basel (CH)

( * ) Notice: Subject to any disclaimer, the term of this patent is extended or adjusted under 35 U.S.C. 154(b) by 143 days.

(21) Appl. No.: 13/865,927

(22) Filed: Apr. 18, 2013

(65) Prior Publication Data

US 2013/0281817 A1    Oct. 24, 2013

Related U.S. Application Data

(60) Provisional application No. 61/635,471, filed on Apr. 19, 2012.

(51) Int. Cl.
*A61B 3/10*        (2006.01)
*A61B 90/00*    (2016.01)
(Continued)

(52) U.S. Cl.
CPC ............ *A61B 3/1005* (2013.01); *A61B 90/06* (2016.02); *A61F 9/00781* (2013.01);
(Continued)

(58) Field of Classification Search
None
See application file for complete search history.

(56) References Cited

U.S. PATENT DOCUMENTS

| | | | |
|---|---|---|---|
| 2,990,670 A | 7/1961 | Kingsbury | |
| 3,439,675 A | 4/1969 | Cohen | |

(Continued)

FOREIGN PATENT DOCUMENTS

| | | |
|---|---|---|
| CN | 1285724 A | 2/2001 |
| EP | 0 228 185 A1 | 11/1986 |

(Continued)

OTHER PUBLICATIONS

Barsky et al. "Evaluation of absorbable gelatin film (Gelfilm) in cyclodialysis clefts" Arch. Ophth. 60(6): 1044-1052,1958.
(Continued)

*Primary Examiner* — Matthew Kremer
(74) *Attorney, Agent, or Firm* — Mintz Levin Cohn Ferris Glovsky and Popeo, P.C.

(57) ABSTRACT

A direct visualization (DV) system and methods are disclosed for measuring one or more anatomical features of the eye, including a depth of the iridocorneal angle of the eye. The DV system can include a wire extending distally from a handle with the wire having one or more indicators for measuring anatomical features of the eye. The DV system can be deployed into the eye and used with minimal trauma to ocular tissues. Furthermore, the DV system can be used independently or alongside other ocular instruments, such as instruments having indicators corresponding to the DV system for correctly implanting ocular implants without the use of a gonio lens.

7 Claims, 8 Drawing Sheets

(51) Int. Cl.
*A61F 9/007* (2006.01)
*A61F 9/008* (2006.01)
*A61F 9/00* (2006.01)

(52) U.S. Cl.
CPC . *A61B 2090/061* (2016.02); *A61B 2090/3735* (2016.02); *A61F 9/0017* (2013.01); *A61F 2009/00891* (2013.01)

(56) References Cited

U.S. PATENT DOCUMENTS

| | | | |
|---|---|---|---|
| 3,767,759 A | 10/1973 | Wichterle | |
| 3,788,327 A | 1/1974 | Donowitz et al. | |
| 3,915,172 A | 10/1975 | Wichterle et al. | |
| 4,037,604 A | 7/1977 | Newkirk | |
| 4,402,681 A | 9/1983 | Haas et al. | |
| 4,457,757 A | 7/1984 | Molteno | |
| 4,521,210 A | 6/1985 | Wong | |
| 4,554,918 A | 11/1985 | White | |
| 4,604,087 A | 8/1986 | Joseph | |
| 4,617,715 A | 10/1986 | Koistinen et al. | |
| 4,634,418 A | 1/1987 | Binder | |
| 4,722,724 A | 2/1988 | Schocket | |
| 4,750,901 A | 6/1988 | Molteno | |
| 4,787,885 A | 11/1988 | Binder | |
| 4,826,478 A | 5/1989 | Schocket | |
| 4,846,172 A | 7/1989 | Berlin | |
| 4,863,457 A | 9/1989 | Lee | |
| 4,886,488 A | 12/1989 | White | |
| 4,900,300 A | 2/1990 | Lee | |
| 4,930,512 A * | 6/1990 | Henriksen ............ A61B 3/1005 600/452 |
| 4,946,436 A | 8/1990 | Smith | |
| 4,968,296 A | 11/1990 | Ritch et al. | |
| 5,041,081 A | 8/1991 | Odrich | |
| 5,071,408 A | 12/1991 | Ahmed | |
| 5,073,163 A | 12/1991 | Lippman | |
| 5,092,837 A | 3/1992 | Ritch et al. | |
| 5,127,901 A | 7/1992 | Odrich | |
| 5,171,213 A | 12/1992 | Price, Jr. | |
| 5,178,604 A | 1/1993 | Baerveldt et al. | |
| 5,180,362 A | 1/1993 | Worst | |
| 5,284,476 A | 2/1994 | Koch | |
| 5,300,020 A | 4/1994 | L'Esperance, Jr. | |
| 5,338,291 A | 8/1994 | Speckman et al. | |
| 5,342,370 A | 8/1994 | Simon et al. | |
| 5,346,464 A | 9/1994 | Camras | |
| 5,370,607 A | 12/1994 | Memmen | |
| 5,372,577 A | 12/1994 | Ungerleider | |
| 5,397,300 A | 3/1995 | Baerveldt et al. | |
| 5,423,777 A | 6/1995 | Tajiri et al. | |
| 5,433,701 A | 7/1995 | Rubinstein | |
| 5,443,505 A | 8/1995 | Wong et al. | |
| 5,454,746 A | 10/1995 | Guegan et al. | |
| 5,476,445 A | 12/1995 | Baerveldt et al. | |
| 5,497,782 A | 3/1996 | Fugoso | |
| 5,558,629 A | 9/1996 | Baerveldt et al. | |
| 5,558,630 A | 9/1996 | Fisher | |
| RE35,390 E | 12/1996 | Smith | |
| 5,601,094 A | 2/1997 | Reiss | |
| 5,626,558 A | 5/1997 | Suson | |
| 5,626,559 A | 5/1997 | Solomon | |
| 5,651,782 A | 7/1997 | Simon et al. | |
| 5,676,944 A | 10/1997 | Alvarado et al. | |
| 5,702,414 A | 12/1997 | Richter et al. | |
| 5,704,907 A | 1/1998 | Nordquist et al. | |
| 5,713,844 A | 2/1998 | Peyman | |
| 5,741,292 A | 4/1998 | Mendius | |
| 5,743,868 A | 4/1998 | Brown et al. | |
| 5,749,879 A | 5/1998 | Middleman et al. | |
| 5,752,928 A | 5/1998 | de Roulhac et al. | |
| 5,792,075 A | 8/1998 | Schwager | |
| 5,807,244 A | 9/1998 | Barot | |
| 5,807,302 A | 9/1998 | Wandel | |
| 5,868,697 A | 2/1999 | Richter et al. | |
| 5,882,327 A | 3/1999 | Jacob | |
| 5,893,837 A | 4/1999 | Eagles et al. | |
| 5,921,918 A | 7/1999 | Riza | |
| 5,941,250 A | 8/1999 | Aramant et al. | |
| 5,968,058 A | 10/1999 | Richter et al. | |
| 6,007,510 A | 12/1999 | Nigam | |
| 6,007,511 A | 12/1999 | Prywes | |
| 6,036,678 A | 3/2000 | Giungo | |
| 6,050,970 A | 4/2000 | Baerveldt | |
| 6,050,999 A | 4/2000 | Paraschac et al. | |
| 6,077,299 A | 6/2000 | Adelberg et al. | |
| 6,102,045 A | 8/2000 | Nordquist et al. | |
| 6,142,969 A | 11/2000 | Nigam | |
| 6,152,918 A * | 11/2000 | Padilla et al. .................. 606/15 |
| 6,174,307 B1 * | 1/2001 | Daniel et al. .................. 606/15 |
| 6,186,974 B1 | 2/2001 | Allan et al. | |
| 6,203,513 B1 | 3/2001 | Yaron et al. | |
| 6,221,078 B1 | 4/2001 | Bylsma | |
| 6,251,090 B1 | 6/2001 | Avery et al. | |
| 6,261,256 B1 | 7/2001 | Ahmed | |
| 6,264,668 B1 | 7/2001 | Prywes | |
| 6,270,472 B1 | 8/2001 | Antaki et al. | |
| 6,331,313 B1 | 12/2001 | Wong et al. | |
| 6,375,642 B1 | 4/2002 | Grieshaber et al. | |
| 6,383,219 B1 | 5/2002 | Telandro et al. | |
| 6,450,984 B1 | 9/2002 | Lynch et al. | |
| 6,464,724 B1 | 10/2002 | Lynch et al. | |
| 6,468,283 B1 | 10/2002 | Richter et al. | |
| 6,471,666 B1 | 10/2002 | Odrich | |
| 6,471,777 B1 | 10/2002 | Kobayashi et al. | |
| 6,494,857 B1 | 12/2002 | Neuhann | |
| 6,508,779 B1 | 1/2003 | Suson | |
| 6,510,600 B2 | 1/2003 | Yaron et al. | |
| 6,524,275 B1 | 2/2003 | Lynch et al. | |
| 6,533,768 B1 | 3/2003 | Hill | |
| 6,537,568 B2 | 3/2003 | Olejnik et al. | |
| 6,544,208 B2 | 4/2003 | Ethier et al. | |
| 6,544,249 B1 | 4/2003 | Yu et al. | |
| 6,558,342 B1 | 5/2003 | Yaron et al. | |
| 6,561,974 B1 | 5/2003 | Grieshaber et al. | |
| 6,579,256 B2 | 6/2003 | Hughes | |
| 6,589,203 B1 | 7/2003 | Mitrev | |
| 6,595,945 B2 | 7/2003 | Brown | |
| 6,626,858 B2 | 9/2003 | Lynch et al. | |
| 6,638,239 B1 | 10/2003 | Bergheim et al. | |
| 6,648,283 B2 | 11/2003 | Chase et al. | |
| 6,666,841 B2 | 12/2003 | Gharib et al. | |
| 6,676,607 B2 | 1/2004 | de Juan, Jr. et al. | |
| 6,699,210 B2 | 3/2004 | Williams et al. | |
| 6,699,211 B2 | 3/2004 | Savage | |
| 6,719,750 B2 | 4/2004 | Varner et al. | |
| 6,726,664 B2 | 4/2004 | Yaron et al. | |
| 6,726,676 B2 | 4/2004 | Stegmann et al. | |
| 6,730,056 B1 | 5/2004 | Ghaem et al. | |
| 6,736,791 B1 | 5/2004 | Tu et al. | |
| 6,741,666 B1 | 5/2004 | Henry et al. | |
| 6,752,753 B1 | 6/2004 | Hoskins et al. | |
| 6,780,164 B2 | 8/2004 | Bergheim et al. | |
| 6,783,544 B2 | 8/2004 | Lynch et al. | |
| 6,786,888 B1 | 9/2004 | Zadno-Azizi et al. | |
| 6,827,699 B2 | 12/2004 | Lynch et al. | |
| 6,827,700 B2 | 12/2004 | Lynch et al. | |
| 6,881,197 B1 | 4/2005 | Nigam | |
| 6,881,198 B2 | 4/2005 | Brown | |
| 6,939,298 B2 | 9/2005 | Brown et al. | |
| 6,955,656 B2 | 10/2005 | Bergheim et al. | |
| 6,962,573 B1 | 11/2005 | Wilcox | |
| 6,966,888 B2 | 11/2005 | Cullen et al. | |
| 6,969,384 B2 | 11/2005 | de Juan, Jr. et al. | |
| 6,981,958 B1 | 1/2006 | Gharib et al. | |
| 6,989,007 B2 | 1/2006 | Shadduck | |
| 7,041,077 B2 | 5/2006 | Shields | |
| 7,090,681 B2 | 8/2006 | Weber et al. | |
| 7,094,225 B2 | 8/2006 | Tu et al. | |
| 7,135,009 B2 | 11/2006 | Tu et al. | |
| 7,160,264 B2 | 1/2007 | Lisk, Jr. et al. | |
| 7,163,543 B2 | 1/2007 | Smedley et al. | |
| 7,186,232 B1 | 3/2007 | Smedley et al. | |
| 7,192,412 B1 | 3/2007 | Zhou et al. | |

(56) References Cited

U.S. PATENT DOCUMENTS

| | | |
|---|---|---|
| 7,195,774 B2 | 3/2007 | Carvalho et al. |
| 7,207,965 B2 | 4/2007 | Simon |
| 7,220,238 B2 | 5/2007 | Lynch et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 | 2/2008 | Tu et al. |
| 7,431,710 B2 | 10/2008 | Tu et al. |
| 7,488,303 B1 | 2/2009 | Haffner et al. |
| 7,563,241 B2 | 7/2009 | Tu et al. |
| 7,708,711 B2 | 5/2010 | Tu et al. |
| 7,850,637 B2 | 12/2010 | Lynch et al. |
| 7,857,782 B2 | 12/2010 | Tu et al. |
| 7,867,186 B2 | 1/2011 | Haffner et al. |
| 7,867,205 B2 | 1/2011 | Bergheim et al. |
| 7,972,616 B2 | 7/2011 | Dubrow et al. |
| 8,075,511 B2 | 12/2011 | Tu et al. |
| 8,172,899 B2 | 5/2012 | Silvestrini et al. |
| 8,337,393 B2* | 12/2012 | Silverstrini et al. .......... 600/104 |
| 8,702,727 B1 | 4/2014 | Harrington et al. |
| 8,721,656 B2 | 5/2014 | De Juan, Jr. et al. |
| 9,155,656 B2 | 10/2015 | Schaller et al. |
| 2002/0013546 A1 | 1/2002 | Grieshaber et al. |
| 2002/0013572 A1 | 1/2002 | Berlin |
| 2002/0072673 A1 | 6/2002 | Yamamoto et al. |
| 2002/0087111 A1 | 7/2002 | Ethier et al. |
| 2002/0111608 A1 | 8/2002 | Baerveldt et al. |
| 2002/0128613 A1 | 9/2002 | Nakayama |
| 2002/0133168 A1 | 9/2002 | Smedley et al. |
| 2002/0143284 A1 | 10/2002 | Tu et al. |
| 2002/0177856 A1 | 11/2002 | Richter et al. |
| 2002/0188282 A1 | 12/2002 | Greenberg |
| 2002/0188308 A1 | 12/2002 | Tu et al. |
| 2002/0193725 A1 | 12/2002 | Odrich |
| 2002/0193804 A1 | 12/2002 | Tickle |
| 2003/0028127 A1 | 2/2003 | Balzum et al. |
| 2003/0028228 A1 | 2/2003 | Sand |
| 2003/0055372 A1 | 3/2003 | Lynch et al. |
| 2003/0060752 A1 | 3/2003 | Bergheim et al. |
| 2003/0097151 A1 | 5/2003 | Smedley et al. |
| 2003/0097171 A1 | 5/2003 | Elliott |
| 2003/0109883 A1* | 6/2003 | Matsuzaki et al. ............. 606/86 |
| 2003/0135149 A1 | 7/2003 | Cullen et al. |
| 2003/0181848 A1 | 9/2003 | Bergheim et al. |
| 2003/0187384 A1 | 10/2003 | Bergheim et al. |
| 2003/0208163 A1 | 11/2003 | Yaron et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0015140 A1 | 1/2004 | Shields |
| 2004/0024345 A1 | 2/2004 | Gharib et al. |
| 2004/0088048 A1 | 5/2004 | Richter et al. |
| 2004/0092856 A1 | 5/2004 | Dahan |
| 2004/0097984 A1 | 5/2004 | Zapata |
| 2004/0102729 A1 | 5/2004 | Haffner et al. |
| 2004/0106977 A1 | 6/2004 | Sullivan et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0148022 A1 | 7/2004 | Eggleston |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225250 A1 | 11/2004 | Yablonski |
| 2004/0236343 A1 | 11/2004 | Taylor et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260228 A1 | 12/2004 | Lynch et al. |
| 2005/0008673 A1 | 1/2005 | Snyder et al. |
| 2005/0049578 A1 | 3/2005 | Tu et al. |
| 2005/0085892 A1 | 4/2005 | Goto et al. |
| 2005/0090806 A1 | 4/2005 | Lynch et al. |
| 2005/0090807 A1 | 4/2005 | Lynch et al. |
| 2005/0101967 A1* | 5/2005 | Weber ..................... A61F 2/167 606/107 |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0119737 A1 | 6/2005 | Bene et al. |
| 2005/0125003 A1 | 6/2005 | Pinchuk et al. |
| 2005/0143817 A1 | 6/2005 | Hunter et al. |
| 2005/0149080 A1 | 7/2005 | Hunter et al. |
| 2005/0171507 A1 | 8/2005 | Christian et al. |
| 2005/0175663 A1 | 8/2005 | Hunter et al. |
| 2005/0181011 A1 | 8/2005 | Hunter et al. |
| 2005/0181977 A1 | 8/2005 | Hunter et al. |
| 2005/0182350 A1 | 8/2005 | Nigam |
| 2005/0191331 A1 | 9/2005 | Hunter et al. |
| 2005/0192527 A1 | 9/2005 | Gharib et al. |
| 2005/0197613 A1 | 9/2005 | Sniegowski et al. |
| 2005/0209549 A1 | 9/2005 | Bergheim et al. |
| 2005/0209550 A1 | 9/2005 | Bergheim et al. |
| 2005/0232972 A1 | 10/2005 | Odrich |
| 2005/0244462 A1 | 11/2005 | Farooq |
| 2005/0245911 A1 | 11/2005 | Wright et al. |
| 2005/0250788 A1 | 11/2005 | Tu et al. |
| 2005/0266047 A1 | 12/2005 | Tu et al. |
| 2005/0267397 A1 | 12/2005 | Bhalla |
| 2005/0267398 A1 | 12/2005 | Protopsaltis et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0283108 A1 | 12/2005 | Savage |
| 2005/0287188 A1 | 12/2005 | Anderson et al. |
| 2005/0288617 A1 | 12/2005 | Yaron et al. |
| 2005/0288619 A1 | 12/2005 | Gharib et al. |
| 2006/0004348 A1 | 1/2006 | Scheller et al. |
| 2006/0020248 A1 | 1/2006 | Prescott |
| 2006/0032507 A1 | 2/2006 | Tu |
| 2006/0036207 A1 | 2/2006 | Koonmen et al. |
| 2006/0069340 A1 | 3/2006 | Simon |
| 2006/0074375 A1 | 4/2006 | Bergheim et al. |
| 2006/0084907 A1 | 4/2006 | Bergheim et al. |
| 2006/0116626 A1 | 6/2006 | Smedley et al. |
| 2006/0149194 A1 | 7/2006 | Conston et al. |
| 2006/0155238 A1 | 7/2006 | Shields |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0235367 A1 | 10/2006 | Takashima et al. |
| 2006/0241580 A1 | 10/2006 | Mittelstein et al. |
| 2006/0241749 A1 | 10/2006 | Tu et al. |
| 2006/0276739 A1 | 12/2006 | Brown |
| 2007/0010827 A1 | 1/2007 | Tu et al. |
| 2007/0088242 A1 | 4/2007 | Coroneo |
| 2007/0088424 A1 | 4/2007 | Greenberg et al. |
| 2007/0088432 A1 | 4/2007 | Solovay et al. |
| 2007/0106235 A1 | 5/2007 | Coroneo |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0129717 A1 | 6/2007 | Brown et al. |
| 2007/0141106 A1 | 6/2007 | Bonutti et al. |
| 2007/0149915 A1 | 6/2007 | Yablonski |
| 2007/0191863 A1 | 8/2007 | De Juan et al. |
| 2007/0207186 A1 | 9/2007 | Scanlon et al. |
| 2007/0233037 A1 | 10/2007 | Gifford et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2008/0015488 A1 | 1/2008 | Tu et al. |
| 2008/0045878 A1 | 2/2008 | Bergheim et al. |
| 2008/0058704 A1 | 3/2008 | Hee et al. |
| 2008/0108933 A1 | 5/2008 | Yu et al. |
| 2008/0147021 A1 | 6/2008 | Jani |

(56) References Cited

U.S. PATENT DOCUMENTS

| | | | |
|---|---|---|---|
| 2008/0151188 A1* | 6/2008 | Kawai | A61B 3/1005 351/206 |
| 2008/0195027 A1 | 8/2008 | Coroneo | |
| 2008/0200860 A1 | 8/2008 | Tu et al. | |
| 2008/0228127 A1 | 9/2008 | Burns et al. | |
| 2008/0234624 A2 | 9/2008 | Bergheim et al. | |
| 2009/0036819 A1 | 2/2009 | Tu et al. | |
| 2009/0036840 A1 | 2/2009 | Viray et al. | |
| 2009/0043321 A1 | 2/2009 | Conston et al. | |
| 2009/0118702 A1 | 5/2009 | Lazar | |
| 2009/0171358 A1* | 7/2009 | Chang et al. | 606/63 |
| 2009/0182421 A1 | 7/2009 | Silvestrini et al. | |
| 2009/0318947 A1 | 12/2009 | Garcia et al. | |
| 2010/0010416 A1 | 1/2010 | Juan, Jr. et al. | |
| 2010/0134759 A1 | 6/2010 | Silvestrini et al. | |
| 2010/0137981 A1 | 6/2010 | Silvestrini et al. | |
| 2010/0152641 A1 | 6/2010 | Yablonski | |
| 2010/0211079 A1 | 8/2010 | Aramant | |
| 2010/0234790 A1 | 9/2010 | Tu et al. | |
| 2010/0268232 A1 | 10/2010 | Betz et al. | |
| 2010/0274259 A1 | 10/2010 | Yaron et al. | |
| 2010/0280317 A1 | 11/2010 | Silvestrini et al. | |
| 2011/0028883 A1 | 2/2011 | Juan, Jr. et al. | |
| 2011/0028884 A1 | 2/2011 | Coroneo | |
| 2011/0087148 A1 | 4/2011 | Silvestrini et al. | |
| 2011/0087149 A1 | 4/2011 | Coroneo | |
| 2011/0087150 A1 | 4/2011 | Coroneo | |
| 2011/0087151 A1 | 4/2011 | Coroneo | |
| 2011/0098629 A1 | 4/2011 | Juan, Jr. et al. | |
| 2011/0098809 A1 | 4/2011 | Wardle et al. | |
| 2011/0112546 A1 | 5/2011 | Juan, Jr. et al. | |
| 2011/0196396 A1 | 8/2011 | Richter et al. | |
| 2011/0238075 A1 | 9/2011 | Clauson et al. | |
| 2011/0276054 A1 | 11/2011 | Helmy | |
| 2011/0288525 A1 | 11/2011 | Hallen et al. | |
| 2011/0306915 A1 | 12/2011 | De Juan, Jr. et al. | |
| 2011/0313271 A1 | 12/2011 | Schulman | |
| 2012/0035524 A1 | 2/2012 | Silvestrini | |
| 2012/0035525 A1 | 2/2012 | Silvestrini | |
| 2012/0046575 A1 | 2/2012 | Brown | |
| 2012/0065670 A1* | 3/2012 | Tiedtke | A61B 17/0057 606/213 |
| 2012/0089071 A1 | 4/2012 | Oliver et al. | |
| 2012/0116504 A1 | 5/2012 | Lyons et al. | |
| 2012/0123316 A1 | 5/2012 | Horvath et al. | |
| 2012/0123433 A1* | 5/2012 | Horvath | A61F 9/0008 606/108 |
| 2012/0123434 A1 | 5/2012 | Grabner et al. | |
| 2012/0271272 A1 | 10/2012 | Hammack et al. | |
| 2014/0155805 A1 | 6/2014 | Schaller et al. | |

FOREIGN PATENT DOCUMENTS

| | | |
|---|---|---|
| EP | 1184010 A2 | 3/2002 |
| EP | 1310222 A2 | 5/2003 |
| EP | 1473004 A2 | 11/2004 |
| EP | 1477146 A2 | 11/2004 |
| EP | 1418868 B1 | 3/2008 |
| EP | 1977724 A1 | 10/2008 |
| EP | 2027837 A2 | 2/2009 |
| GB | 2101891 A | 1/1983 |
| JP | 2007-535386 A | 12/2007 |
| JP | 2010-533565 A | 10/2010 |
| RU | 2018289 C1 | 8/1994 |
| RU | 2056818 C1 | 3/1996 |
| RU | 2074686 C1 | 3/1997 |
| RU | 2074687 C1 | 3/1997 |
| RU | 2157678 C1 | 10/2000 |
| RU | 2010121933 A | 12/2011 |
| WO | WO-89/00869 A1 | 2/1989 |
| WO | WO-91/12046 A1 | 8/1991 |
| WO | WO-92/19294 A1 | 11/1992 |
| WO | WO-94/02081 A1 | 2/1994 |
| WO | WO-94/09721 A1 | 5/1994 |
| WO | WO-94/09837 A1 | 5/1994 |
| WO | WO-94/13234 A1 | 6/1994 |
| WO | WO-95/08310 A1 | 3/1995 |
| WO | WO-95/13765 A1 | 5/1995 |
| WO | WO-96/20742 A1 | 7/1996 |
| WO | WO-96/36377 A1 | 11/1996 |
| WO | WO-97/44085 A2 | 11/1997 |
| WO | WO-98/23237 A1 | 6/1998 |
| WO | WO-98/30181 A1 | 7/1998 |
| WO | WO-99/26567 A1 | 6/1999 |
| WO | WO-00/06223 A1 | 2/2000 |
| WO | WO-00/64389 A1 | 11/2000 |
| WO | WO-00/64390 A1 | 11/2000 |
| WO | WO-00/64391 A1 | 11/2000 |
| WO | WO-00/64393 A1 | 11/2000 |
| WO | WO-00/64511 A1 | 11/2000 |
| WO | WO-01/78631 A2 | 10/2001 |
| WO | WO-01/78656 A2 | 10/2001 |
| WO | WO-01/97727 A1 | 12/2001 |
| WO | WO-02/36052 A1 | 5/2002 |
| WO | WO-02/070045 A1 | 9/2002 |
| WO | WO-02/074052 A2 | 9/2002 |
| WO | WO-02/080811 A2 | 10/2002 |
| WO | WO-02/080829 A2 | 10/2002 |
| WO | WO-02/087418 A2 | 11/2002 |
| WO | WO-02/087479 A2 | 11/2002 |
| WO | WO-02/089699 A2 | 11/2002 |
| WO | WO-02/102274 A2 | 12/2002 |
| WO | WO-03/015659 A2 | 2/2003 |
| WO | WO-03/015667 A1 | 2/2003 |
| WO | WO-03/041622 A2 | 5/2003 |
| WO | WO-03/073968 A2 | 9/2003 |
| WO | WO-03/096871 A2 | 11/2003 |
| WO | WO-03/099175 A1 | 12/2003 |
| WO | WO-2004/014218 A2 | 2/2004 |
| WO | WO-2004/026106 A2 | 4/2004 |
| WO | WO-2004/026347 A2 | 4/2004 |
| WO | WO-2004/043231 A2 | 5/2004 |
| WO | WO-2004/056294 A1 | 7/2004 |
| WO | WO-2004/060219 A1 | 7/2004 |
| WO | WO-2004/062469 A2 | 7/2004 |
| WO | WO-2004/073552 A2 | 9/2004 |
| WO | WO-2004/110391 A2 | 12/2004 |
| WO | WO-2005/016418 A1 | 2/2005 |
| WO | WO-2005/046782 A1 | 5/2005 |
| WO | WO-2005/055873 A2 | 6/2005 |
| WO | WO-2005/105197 A2 | 11/2005 |
| WO | WO-2005/107664 A2 | 11/2005 |
| WO | WO-2005/107845 A1 | 11/2005 |
| WO | WO-2006/012421 A2 | 2/2006 |
| WO | WO-2006/036715 A2 | 4/2006 |
| WO | WO-2007/087061 A2 | 8/2007 |
| WO | WO-2007/115259 A2 | 10/2007 |
| WO | WO-2007/130393 A2 | 11/2007 |
| WO | WO-2008/061043 | 5/2008 |
| WO | WO-2009/012406 A1 | 1/2009 |
| WO | WO-2009/035562 A2 | 3/2009 |
| WO | WO-2009/058929 A1 | 5/2009 |
| WO | WO-2009/158524 A2 | 12/2009 |
| WO | WO-2010/065970 A1 | 6/2010 |
| WO | WO-2010/115101 A1 | 10/2010 |
| WO | WO-2012/019136 A2 | 2/2012 |

OTHER PUBLICATIONS

Bick MW "Use of tantalum for ocular drainage" Arch Ophthal. 42(4): 373-88 (1949).

Bietti "The present state of the use of plastics in eye surgery" Acta Ophthalmol (Copenh) 33(4):337-70 (1955).

Brown et al., "Internal Sclerectomy for Glaucoma Filtering Surgery with an Automated Trephine," Archives of Ophthalmology, 105:133-136 (1987).

Burchfield JC, Kass MA, Wax MB. Primary valve malfunction of the Krupin eye valve with disk. J Glaucoma. Jun. 1997;6(3):152-6.

Chiou et al. "Ultrasound biomicroscopy of eyes undergoing deep sclerectomy with collagen implant" Br J Ophthalmol 80 (1996), pp. 541-544.

(56) References Cited

OTHER PUBLICATIONS

Chylack LT, Bellows AR. Molecular sieving in suprachoroidal fluid formation in man. Invest Ophthalmol Vis Sci 17: 420, 1978.

Classen et al. "A histopathologic and immunohistorchemical analysis of the filtration bleb after unsuccessful glaucoma seton implantation" Am. J. Ophthalmol. 122:205-12 (1996).

Cohen et al. "First day post-operative review following uncomplicated phacoemulsification" Eye 12(4):634-6 (1998).

Collaborative Normal-Tension Study Group. Comparison of glaucomatous progression between untreated patients with normal-tension glaucoma and patients with therapeutically reduced intraocular pressures. Am J Ophthalmol 1998;126:487-97.

Congdon N, O'Colmain B, Klaver CC, et al. Causes and prevalence of visual impairment among adults in the United States. Arch Ophthalmol 2004;122:477-85.

Coote. "Glaucoma Hollow Fiber Filters—A New Glaucoma Seton. Preliminary Results." *J. Glaucoma.* vol. 8 No. 1 Supplement (1999):p.54.

Cullen, et al. "Anterior Chamber of Frontal Sinus Shunt for the Diversion of Aqueous Humor: A Pilot Study in Four Normal Dogs". *Veterinary Ophthalmology.* vol. 1. No. 1. (1998):31-39.

Demailly et al. "Non-penetrating deep sclerectomy (NPDS) with or without collagen device (CD) in primary open-angle glaucoma: middle-term retrospective study" International Ophthalmology 20: 131-140, 1997.

Derwent English abstract for EP 1184010, published Mar. 6, 2002 entitled: "Drainage unit for an eye, consists of a hollow line, a distribution member, and a pressure relief valve which only allows water to leave the eye chamber above a certain pressure," Accession Nbr. 12409716 [351].

Dinakaran et al. "Is the first post-operative day review necessary following uncomplicated hacoemulsification surgery?" Eye, 14(3A):364-6 (2000).

Draeger "Chirurgische Maßnahmen bei kongenitalem Glaukom" (Surgical Interventions in Congenital Glaucoma) Klin Monatsbl Augenheilkd 1993; 202(5): 425-427 [Article in German with English summary included]

Einmahl et al. "Evaluation of a novel biomaterial in the suprachoroidal space of the rabbit eye" Invest Ophthalmol Vis Sci. 43:1533-1539 (2002).

Ellis, RA "A Reduction of Intraocular Pressure Using Plastics in Surgery" Am J Ophth. 50; 1960, 733-742.

Emi et al. "Hydrostatic pressure of the suprachoroidal space" Invest. Ophthal. Visual Sci. 30(2):233-238 (1989).

Fanous MM, Cohn RA. Propionibacterium endophthalmitis following Molteno tube repositioning. J Glaucoma. Aug. 1997;6(4):201-2.

Friedman DS, Wolfs RC, O'Colmain BJ, et al. Prevalence of open-angle glaucoma among adults in the United States. Arch Ophthalmol 2004;122:532-8.

Fuchs E. "Detachment of the choroid inadvertently during cataract surgery" [German] von Graefes Arch Ophthalmol, 51:199-224 (1900) [Article in German with English summary].

Gills et al. "Action of cyclodialysis utilizing an implant studied by manometry in a human eye" Exp Eye Res 1967; 6:75-78.

Gills JP "Cyclodialysis implants" South Med J. 1967 60(7):692-5.

Gills, "Cyclodialysis Implants in Human Eyes" Am J Ophth 61:1966,841-846.

Goldberg "Management of Uncontrolled Glaucoma With the Molteno System" Australian and New Zealand Journal of Ophthalmology 1987; 15: 97-107.

Gordon MO, Kass. MA, for the Ocular Hypertension Treatment Study Group. The Ocular Hypertension Treatment Study. Design and baseline description of the participants. Arch Ophthalmol 1999:573-83.

Grant, W.M. , MD, Further Studies on Facility of Flow Through the Trabecular Meshwork, A.M.A. Archives of Ophthalmololgy, Oct. 1958, vol. 60, pp. 523-533.

Gross et al. "Surgical therapy of chronic glaucoma in aphakia and pseudophakia" Ophthalmology, 95:1195-201 (1988).

Harper SL, Foster CS. Intraocular lens explantation in uveitis. Int Ophthalmol Clin. 2000 Winter; 40(1):107-16.

Harrington "Cataract and Glaucoma. Management of the coexistent conditions and a description of a new operation combining lens extraction with reverse cyclodialysis." Am J Ophthalmol. May 1966;61(5 Pt 2):1134-40.

Heijl A, Leske MC, Bengtsson B, et al for the Early Manifest Glaucoma Trial Group. Reduction of intraocular pressure and glaucoma progression. Results from the Early Manifest Glaucoma Trial. Arch Ophthalmol 2002;120:1268-79.

Heine I. "Cyclodialysis, a new glaucoma operation" [German] Dtsch Med Wochenschr, 31:824-826 (1905).

Hildebrand et al. "Efficacy of anterior chamber decompression in controlling early intraocular pressure spikes after uneventful phacoemulsification" J. Catact Refract Surg., 29:1087-92 (2003).

Hoskins, et al., "Aqueous Humor Outflow", Becker-Shaffer's Diagnosis and Therapy of the Glaucomas, 6th Edition, Chapter 4, pp. 41-66, 1989.

Howorth D J "Feasibility study for a micromachined glaucoma drainage device" Cranfield University School of industrial and manufacturing science MSc Thesis Academic Year 2001-2002 Sep. 13, 2002.

Hylton et al. "Update on prostaglandin analogs" Curr Opin Ophthalmol, 14:65-9 (2003).

Javitt JC, Chiang YP. Preparing for managed competition. Utilization of ambulatory eye care visits to ophthalmologists. Arch Ophthalmol 1993;111:1034-5.

Jay JL, Allan D. The benefit of early trabeculectomy versus conventional management in primary open-angle glaucoma relative to severity of disease. Eye 1989; 3:528-35.

Jordan J. "A Novel Approach to Suprachoroidal Drainage for the Surgical Treatment of Intractable Glaucoma" J. Glaucoma 15:200-205 (2006).

Jordan JF, Dietlein TS, Dinslage S, Luke C, Konen W, Krieglstein GK. Cyclodialysis ab inferno as a surgical approach to intractable glaucoma. Graefes Arch Clin Exp Ophthalmol. Aug. 2007;245(8):1071-6.

Karlen et al. "Deep sclerectomy with collagen implant: medium term results" Br. J. Ophthalmol, Jan. 1999, 83(1):6-11.

Kass MA, Heuer DK, Higginbotham EJ, et al for the Ocular Hypertension Treatment Study Group. The Ocular Hypertension Treatment Study. A randomized trial determines that topical ocular hypotensive medication delays or prevents the onset of primary open-angle glaucoma. Arch Ophthalmol 2002;120:701-13.

Klemm et al. "Die Ultraschallbiomikroskopie als Kriterium der Funktionsprüfung des suprachorioidalen Spaltes nach kammerwinkelchirurgischen Eingriffen" (Ultrasound Biomicroscopic Imaging for Assessment of the Suprachoroidal Cleft after Angle Surgery)"Klinische Monatsblätter für Augenheilkunde 1997; 210: 74-77 [Article in German with English summary included]".

Klemm et al. "Experimental use of space-retaining substances with extended duration: functional and morphological results" Graefes Arch Clin Exp Ophthalmol Sep. 1995; 233(9):592-7.

Kozlov et al. "Nonpenetrating deep sclerectomy with collagen" Eye microsurgery 3:44-46 (1990) [Russian with English translation].

Krejci "Cyclodialysis with hydroxymethyl methacrylate capillary strip (HCS). Animal experiments with a new approach in glaucoma drainage surgery" Ophthalmologica 1972; 164(2):113-21.

Krejci L. "Microdrainage of anterior chamber of eye glaucoma operation using hydron capillary drain. " Acta Univ Carol Med Monogr. 1974;(61):1-90.

Kupfer "Studies on intraocular pressure. I. A technique for polyethylene tube implantation into the anterior chamber of the rabbit. " Arch Ophthalmol. Apr. 1961;65:565-70.

La Rocca "Gonioplasty in Glaucoma a Preliminary Report" Br J Ophth 46:1962, 404-415.

Law et al., "Retinal Complications After Aqueous Shunt Surgical Procedures for Glaucoma" Arch Ophthal.; Dec. 1996; vol. 114:1473-1480.

Lee et al. "Aqueous-venous shunt and intraocular pressure. Preliminary report of animal studies." *Investigative Ophthalmology.* vol. 5 No. 1:59-64. Feb. 1966.

(56) References Cited

OTHER PUBLICATIONS

Lee et al. "Magnetic resonance imaging of the aqueous flow in eyes implanted with the trabeculo-suprachoroidal glaucoma seton" Invest. Ophthalmol. Vis. Sci. 33:948 (1992).
Lee KY. Trabeculo-suprachoroidal shunt for treating recalcitrant and secondary glaucoma. Presented at the American Academy of Ophthalmology Annual Meeting, Anaheim, CA, 1991.
Leske MC, Heijl A, Hussein M, et al for the Early Manifest Glaucoma Trial Group. Factors for glaucoma progression and the effect of treatment. The Early Manifest Glaucoma Trial. Arch Ophthalmol Jan. 2003;121:48-56.
Lichter PR, Musch DC, Gillespie BW, et al and the CIGTS Study Group. Interim clinical outcomes in the Collaborative Initial Glaucoma Treatment Study comparing initial treatment randomized to medications or surgery. Ophthalmology 2001;108:1943-53.
Losche W. "Proposals for improvement of cyclodialysis" Klin Monatsblatter Augenheilkd Augenarztl Fortbild 121(6):715-6 (1952) [German].
Marx et al., "Use of the Ganciclovir Implant in the Treatment of Recurrent Cytomegalovirus Retinitis" Arch Ophthal.; Jul. 1996; vol. 114:815-820.
McPherson "Combined Trabeculotomy and Cataract Extraction as a Single Operation" Tr. Am. Ophth. Soc., vol. LXXIV, 1976; 251-260.
Migdal C, Gregory W, Hitchings R. Long term functional outcome after early surgery compared with laser and medicine in open-angle glaucoma. Ophthalmology 1994;101:1651-7.
Miglior S, Pfeiffer N, Zeyen T et al for the European Glaucoma Prevention Study Group. Results of the European Glaucoma Prevention Study. Ophthalmology 2005;112:366-75.
Miglior S, Zeyen T, Pfeiffer N, et al for the European Glaucoma Prevention Study Group. The European Glaucoma Prevention Study design and baseline description of the participants. Ophthalmology 2002;109:1612-21.
Miki, MD et al., "Intraocular Cannula for Continuous, Chronic Drug Delivery-Histopathic Observations and Function" Arch Ophthal.; May 1985; vol. 103:712-717.
Molteno et al. "Long tube implants in the management of glaucoma" South African Medical Journal, Jun. 26, 1976;50(27):1062-6.
Molteno et al. "The Vicryl tie technique for inserting a draining implant in the treatment of secondary glaucoma. " Australian and New Zealand Journal of Ophthalmology 1986; 14: 343-354.
Moses RA "Detachment of ciliary body-anatomical and physical considerations" Investigative Ophthalmology & Visual Science, Assoc. for Research in Vision and Ophthalmology, US, vol. 4, No. 5, Oct. 1, 1965.
Nesterov AP et al. "Surgical stimulation of the uveoscleral outflow. Experimental studies on enucleated human eyes" Acta Opthalmol (Copenh) June; 57(3):409-17 (1979).
Nguyen et al., "Complications of Baerveldt Glaucoma Drainage Implants" Arch Ophthal.; May 1998; vol. 116:571-575.
Noecker RJ. Clinical Evaluation of a Novel Gold Micro-Shunt for Reduction of 10 P in Refractory Glaucomas. American Glaucoma Society Annual Meeting, San Francisco, CA, 2007.http://www.glaucomaweb.org/associations/5224/files/AGS%20AM07%20Prgrm%20FINAL.pdf. Accessed Nov. 1, 2008).
O'Brien et al. "Cyclodialysis" Arch Ophthal. 1949;42(5):606-619.
Odrich. "The New Technique During Complex Tube-Shunt Implantation". J. Glaucoma. vol. 9 No. 3 (2000):278-279.
Olsen, Timothy W., et al., Cannulation of the Suprachoroidal Space: A Novel Drug Delivery Methodology to the Posterior Segment, American Journal of Ophthalmology, vol. 142, No. 5, Nov. 2006, pp. 777-787.e2.
Ozdamar et al. "Suprachoroidal seton implantation in refractory glaucoma: a novel surgical technique" J. Glaucoma Aug. 2003; 12(4):354-9.
Pinnas G. et al. "Cyclodialysis with teflon tube implants" Am J. Ophthalmol Nov. 1969; 68(5):879-883.
Portney GL, "Silicone elastomer implantation cyclodialysis." Arch Ophthalmol 1973; 89: 10-12.

Primary Open Angle Glaucoma. Preferred Practice Patterns, American Academy of Ophthalmology.http://one.aao.org/CE/PracticeGuidelines/PPP_Content.aspx?cid=a5a59e02-450b-4d50-8091-b2dd2lefl ff2#references (Accessed Nov. 1, 2008).
Pruett et al., "The Fishmouth Phenomenon-II. Wedge Scleral Buckling" Arch Ophthal.; Oct. 1977; vol. 95:1782-1787.
Qadeer "Acrylic Gonio-Subconjunctival Plates in Glaucoma Surgery " Br J Ophthalmol. Jun. 1954; 38(6): 353-356.
Quigley HA, Vitale S. Models of open-angle glaucoma prevalence and incidence in the United States. Invest Ophthalmol Vis Sci 1997; 38:83-91.
Richards et al. "Artificial Drainage Tubes for Glaucoma" Am J Ophth 60:1965,405-408.
Ritch, et al., "Uveoscleral Outflow", the Glaucomas. St. Louis: Mosby, 1996; pp. 337-343.
Rohen, Johannes W., Anatomy of the Aqueous Outflow Channels, Glaucoma, vol. 1, Chapter 14, pp. 277-296, Edited by J.E. Cairns, Grune & Stratton, Harcourt Brace Jovanovich Publishers, 1986.
Rosenberg, et al. "Implants in glaucoma surgery" Chapter 88, the Glaucomas, Ritch et al. Eds. 2nd Ed. Mosby St. Louis 1996; p. 1783-1807.
Row H. "Operation to control glaucoma: preliminary report" Arch. Ophthal 12:325 (1934).
Rowan, Patrick J., MD, Combined Cyclodialysis and Cataract Surgery, Ophthalmic Surgery and Lasers, Dec. 1998, vol. 29, No. 12, pp. 962-968 (9 pages).
Sampimon "A New Approach to Filtering Glaucoma Surgery" Ophthalmologica (Basel) 151: 1966, 637-644.
Schappert S. Office visits for glaucoma: United States, 1991-92. Advance data from vital and health statistics. vol. 262. Hyattsville, MD: National Center for Health Statistics, 1995.
Shaffer RN, Weiss DI. Concerning cyclodialysis and hypotony. Arch Ophthalmol 68: 25, 1962.
SOLX Clinical Literature Handout; Industry Show Feb. 2006; "The SOLX Gold Micro-shunt (GMS) treatment".
Sommer A, Tielsch JM, Katz J, et al. Racial differences in the cause-specific prevalence of blindness in east Baltimore. N Engl J Med 1991;325:1412-7.
Sourdille et al. "Reticulated hyaluronic acid implant in non-perforating trabecular surgery." J Cataract Refract Surg 25: 332-339. (1999).
Spiegel et al. "Schlemm's Canal Implant: A New Method to Lower Intraocular Pressure in Patients With POAG?" Ophthalmic Surgery and Lasers. vol. 30, No. 6: 492-494. Jun. 1999.
Srinivasan et al. "Microbial contamination of the anterior chamber during phacoemulsification" J. Cataract Refract Surg. 28:2173-6 (2002).
Suguro K, Toris CB, Pederson JE. Uveoscleral outflow following cyclodialysis in the monkey eye using a fluorescent tracer. Invest Ophthalmol Vis Sci 1985: 26, 810.
The Advanced Glaucoma Intervention Study (AGIS): 7. The relationship between control of intraocular pressure and visual field deterioration. The AGIS Investigators. Am J Ophthalmol 2000;130:429-40.
The Advanced Glaucoma Intervention Study (AGIS); 13. Comparison of treatment outcomes within race: 10-year results. Ophthalmology 2004;111:651-64.
The Glaucoma Laser Trial (GLT) and Glaucoma Laser Trial Follow-up Study: 7. Results. Am J Ophthahnol 1995;120:718-31.
The Glaucoma Laser Trial (GLT). 2. Results of argon laser trabeculoplasty versus topical medicines. The Glaucoma Laser Trial Research Group. Ophthalmology 1990;97:1403-13.
Thiagalingam S, Tarongoy P, Hamrah P, Lobo AM, Nagao K, Barsam C, Bellows R, Pineda R. Complications of cosmetic iris implants. J Cataract Refract Surg. Jul. 2008;34(7):1222-4.
Tielsch JM, Sommer A, Katz J, et al. Racial variations in the prevalence of primary open-angle glaucoma. The Baltimore Eye Survey. JAMA 1991;266:369-74.
Toris CB. Extravascular albumin concentration of the uvea. Invest Ophthalmol Vis Sci 1990; 31:43.
Toris et al. "Aqueous humor dynamics in the aging human eye" Am J. Ophthalmol., 127:407-12 (1999).

(56) References Cited

OTHER PUBLICATIONS

Toris et al. "Effect of intraocular pressure on uveoscleral outflow following cyclodialysis in the monkey eye." Investigative Ophthalmology & Visual Science. 26 (1985) 1745-1749.
Trigler L, Proia AD, Freedman SF. Fibrovascular ingrowth as a cause of Ahmed glaucoma valve failure in children. Am J Ophthalmol. Feb. 2006;141(2):388-9.
Troncoso Manuel U., "Cyclodialysis with insertion of metal implant in treatment of glaucoma, a Preliminary Report" Arch. Ophthal. 23:270 (1940).
Troncoso, Manuel U., Tantalum implants for inducing hypotny, Am Journal of Ophthalmology, vol. 32(4):499-508 (1949).
Van der Veen et al. "The gonioseton, a surgical treatment for chronic glaucoma". Documenta Ophthalmologica; vol. 75, Nos. 3-4, 365-375. (1990).
Vossmerbaeumer U, Ditzen K, Jonas JB. Removal of an intracorneal hydrogel implant for hyperopia after Lasik. J Refract Surg. Jan. 2007;23(1):102-4.
Wagner, Justin A., et al., Characterization of Uveoscleral Outflow in Enucleated Porcine Eyes Perfused under Constant Pressure, Invest Ophthalmol Vis Sci., Published in edited form in Sep. 2004, vol. 45, Issue 9, pp. 3203-3206.
Wamsley S, Moster MR, Rai S, Alvim HS, Fontanarosa J. Results of the use of the Ex-Press miniature glaucoma implant in technically challenging, advanced glaucoma cases: a clinical pilot study. Am J Ophthalmol. Dec. 2004; 138(6): 1049-51.
Yablonski, "Some thoughts on the pressure dependence of uveoscleral flow" Journal of Glaucoma, 12(1):90-92 (2003).
Yablonski, "Trabeculectomy with Internal Tube Shunt: a novel glaucoma surgery" J. Glaucoma 14:91-97 (2005).
Yoo C, Kwon SW, Kim YY. Pericardium plug in the repair of the corneoscleral fistula after ahmed glaucoma valve explantation. Korean J Ophthalmol. Dec. 2008;22(4):268-71.
Zhou et al. "A trabecular bypass flow hypothesis" J Glaucoma. 14(1):74-83 (2005).
Schocket, Stanley S. "Investigations of the Reasons for Success and Failure in the Anterior Shunt-to-the-Encircling-Band Procedure in the Treatment of Refractory Glaucoma." Tr. Am. Ophth. Soc.vol. LXXXIX. (1986):743-798.
U.S. Appl. No. 13/365,175, filed Feb. 2, 2012, 2012-0220917.
U.S. Appl. No. 14/025,145, filed Sep. 12, 2013, 2014-0012279.
U.S. Appl. No. 14/029,389, filed Sep. 17, 2013, 2014-0081195.
U.S. Appl. No. 14/071,500, filed Nov. 4, 2013. 2014-0066831.
U.S. Appl. No. 14/078,206, filed Nov. 12, 2013, 2014-0135916.
U.S. Appl. No. 14/140,322, filed Dec. 24, 2013, 2014-0107556.
U.S. Appl. No. 14/163,364, filed Jan. 24, 2014, 2014-0213958.
U.S. Appl. No. 14/260,041, filed Apr. 23, 2014, 2014-0323995.
U.S. Appl. No. 14/283,759, filed May 21, 2014, 2014-0364789.
U.S. Appl. No. 14/466,863, filed Aug. 22, 2014, 2014-0378886.
U.S. Appl. No. 14/610,197, filed Jan. 30, 2015, 2015-0223982.
U.S. Appl. No. 14/706,893, filed May 7, 2015, 2015-0238360.
U.S. Appl. No. 14/804,008, filed Jul. 20, 2015, 2015-0320596.
U.S. Appl. No. 14/809,827, filed Jul. 27, 2015, 2016-0022486.
U.S. Appl. No. 14/817,600, filed Aug. 4, 2015, 2015-0335487.
U.S. Appl. No. 14/971,542, filed Dec. 16, 2015, 2016-0175152.
U.S. Appl. No. 14/987,133, filed Jan. 14, 2016, 2016-0193083.
U.S. Appl. No. 15/005,745, filed Jan. 25, 2016, 2016-0135992.

\* cited by examiner

DIRECT VISUALIZATION SYSTEM FOR GLAUCOMA TREATMENT

REFERENCE TO PRIORITY DOCUMENT

This application claims priority benefit under 35 U.S.C. § 119(e) of U.S. Provisional Patent Application Ser. No. 61/635,471, filed Apr. 19, 2012, and entitled "Direct Visualization System for Glaucoma Treatment." The priority of the filing date of Apr. 19, 2012 is hereby claimed, and the disclosure of the provisional patent application is hereby incorporated by reference in its entirety.

BACKGROUND

The mechanisms that cause glaucoma are not completely known. It is known that glaucoma results in abnormally high pressure in the eye, which leads to optic nerve damage. Over time, the increased pressure can cause damage to the optic nerve, which can lead to blindness. Treatment strategies have focused on keeping the intraocular pressure down in order to preserve as much vision as possible over the remainder of the patient's life.

Pursuant to such strategies, one or more implants can be delivered into the eye for shunting fluid out of the anterior chamber in order to regulate pressure in the eye. Accurate placement of an implant in the angle of the eye is critical for the targeted effect of reducing intraocular pressure (IOP). Placing an implant too distally into the eye, such as too distally into the supraciliary space, may leave no portion of the implant remaining in the anterior chamber. This may inhibit aqueous outflow, as the fluid will not have a direct communication with the flow target location if there is no opening to the anterior chamber.

Conversely if the implant is placed too proximally in the supraciliary space such that a significant portion of the implant remains in the anterior chamber, damage to the corneal endothelium may result from implants that protrude upwards and touch the cornea. Implants placed too proximally may also touch the iris resulting in increased amounts of pigment dispersion in the eye, which can increase outflow resistance and intraocular pressure by clogging the trabecular meshwork. Correct placement of the implant is desired for a safety and a successful surgical outcome.

Many surgical procedures in ophthalmology require visualization of the iridocorneal angle (sometimes referred to as "the angle") of the eye. Current techniques include endoscopy and gonioscopy, though both require clinicians to use at least two hands during surgery. This can be cumbersome for the surgeon. Surgical procedures that primarily involve the measurement of the depth of the angle, such as many minimally invasive glaucoma surgeries (MIGS), may benefit from a simplified method of placing implants in the angle of the eye particularly with respect to visualization of the iridocorneal angle.

Proper placement of ophthalmic implants in the angle of the eye can be critical to implant performance. Current visualization techniques may provide satisfactory angle visualization, although current techniques suffer from a multitude of issues. Gonioscopy requires the clinician to use an additional hand during surgery and the gonio lens must be placed directly on the cornea, increasing risk of infection and corneal damage. The surgical microscope used during gonioscopy may also require adjustment for proper angle visualization, which adds to surgery time. Endoscopy also requires the clinician to use an additional hand during surgery and a may involve a larger or second limbal incision for access to the anterior chamber, increasing the potential for surgical complications such as hypotony. Additionally, these techniques are not intuitive to many physicians and require significant training.

In view of the foregoing, there is a need for direct visualization (DV) systems which are configured and adapted for measuring a depth of the iridocorneal angle of the eye. In addition, there is a need for the DV systems to deploy into the eye and be used with minimal trauma to ocular tissues.

SUMMARY

There is a need for improved systems, devices and methods for the treatment of diseases, such as glaucoma.

In a first embodiment, disclosed herein is a device for measuring anatomical features of an eye. The device can include a handle and a wire including a contact tip at a distal end of the wire. In addition, the wire can extend out of the handle and can be configured to be inserted ab-internally and positioned against ocular tissue in the eye. The wire can include at least one indicator for assisting in measuring at least one anatomical feature of the eye.

Also described herein are methods of measuring anatomical features of an eye and implanting an ocular implant. In an embodiment, disclosed is a method including forming an incision in the cornea of the eye into an anterior chamber of the eye. The method can also include introducing through the incision a distal end of a device for measuring at least one anatomical feature of the eye. The device can comprise a handle with a wire extending out of a distal end of the handle. In addition, a distal end of the wire can be configured to be pressed against ocular tissue in the eye. The wire can include at least one indicator for measuring at least one anatomical feature of the eye. The method can also include passing the distal end of the wire through the incision and across the anterior chamber of the eye and positioning the distal end of the wire against ocular tissue below the scleral spur and above the iris. The method can also include measuring at least one anatomical feature of the eye by identifying one or more indicators along a length of the wire relative to one or more anatomical features.

Other features and advantages should be apparent from the following description of various embodiments, which illustrate, by way of example, the principles of the described subject matter.

BRIEF DESCRIPTION OF THE DRAWINGS

These and other aspects will now be described in detail with reference to the following drawings.

Like reference symbols in the various drawings indicate like elements.

DETAILED DESCRIPTION

Disclosed is a direct visualization (DV) system configured and adapted for measuring a depth of the iridocorneal angle of the eye. The system is configured to be deployed into the eye and used with minimal trauma to ocular tissues. The system includes a direct visualization (DV) wire with indicators, such as numbers or patterns that indicate or represent known distances. In use, the DV wire can be placed directly against the base of the iridocorneal angle allowing for depth measurements. The system can further include a spring connected to the DV wire. In addition, the spring can have a very low spring constant. The spring can allow the DV wire to abut against the tissues in the eye with low contact force. Such a system may be used independently or alongside other ocular instruments, such as instruments having indicators corresponding to the DV system for correctly implanting ocular implants without the use of a gonio lens.

The disclosed system provides reduced or minimal risk of damaging ocular tissue and has several advantageous qualities over current visualization techniques. The disclosed system requires only one limbal incision, which may be on the scale of 1.0-2.5 mm. For cases where the DV system is used alongside another tool with matching calibrated depth measuring features, the same limbal incision may be used for both the DV system and the additional tool. Once inside the anterior chamber the DV system can interact solely with the aqueous humor and tissues comprising the angle of the eye.

Figure 1:
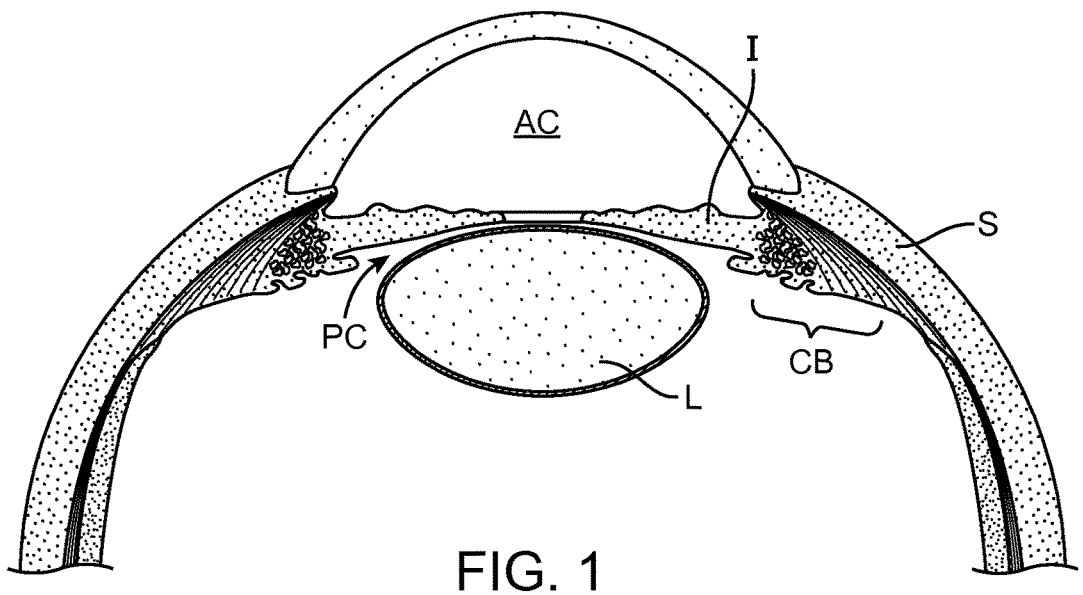
FIG. 1 shows an example cross-sectional view of a portion of the human eye.

FIG. 1 is a cross-sectional view of a portion of the human eye. The eye is generally spherical and is covered on the outside by the sclera S. The retina lines the inside posterior half of the eye. The retina registers the light and sends signals to the brain via the optic nerve. The bulk of the eye is filled and supported by the vitreous body, a clear, jelly-like substance. The elastic lens L is located near the front of the eye. The lens L provides adjustment of focus and is suspended within a capsular bag from the ciliary body CB, which contains the muscles that change the focal length of the lens. A volume in front of the lens L is divided into two by the iris I, which controls the aperture of the lens and the amount of light striking the retina. The pupil is a hole in the center of the iris I through which light passes. The volume between the iris I and the lens L is the posterior chamber PC. The volume between the iris I and the cornea is the anterior chamber AC. Both chambers are filled with a clear liquid known as aqueous humor.

The ciliary body CB continuously forms aqueous humor in the posterior chamber PC by secretion from the blood vessels. The aqueous humor flows around the lens L and iris I into the anterior chamber and exits the eye through the trabecular meshwork, a sieve-like structure situated at the corner of the iris I and the wall of the eye (the corner is known as the iridocorneal angle). Some of the aqueous humor can filter through the trabecular meshwork near the iris root into Schlemm's canal, a small channel that drains into the ocular veins. A smaller portion rejoins the venous circulation after passing through the ciliary body and eventually through the sclera (the uveoscleral route).

Figure 2:
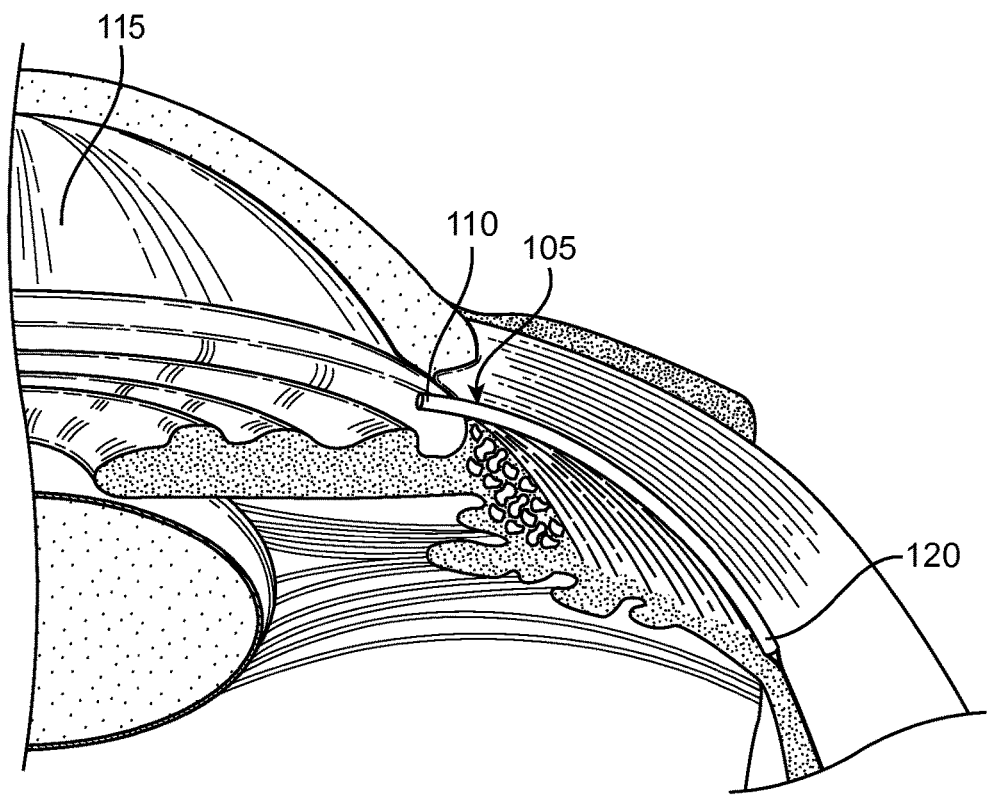
FIG. 2 shows and an example partial cross-sectional view of the eye showing a part of the anterior and posterior chambers of the eye and an ocular implant implanted in the eye.

FIG. 2 is a cross-sectional, perspective view of a portion of the eye showing the anterior and posterior chambers of the eye. A schematic representation of an embodiment of an implant 105 is shown positioned inside the eye such that a proximal end 110 is located in the anterior chamber 115 and a distal end 120 communicates with and/or is located in or near the suprachoroidal space. It should be appreciated that FIG. 1 and other figures herein are schematic and are not necessarily to scale with respect to size and relative positions of actual eye tissue. Prior to insertion and implantation of an implant, such as the implant shown in FIG. 2, it can be beneficial to first measure the angle of the eye. For example, measuring the angle of the eye can assist in determining the proper size and shape of the implant for implantation, as well as the proper placement of the implant in the eye. At least one benefit of the DV system embodiments disclosed herein includes the ability to assist in determining the proper size and shape of implant as well as properly placing an implant in the eye.

Figure 3:
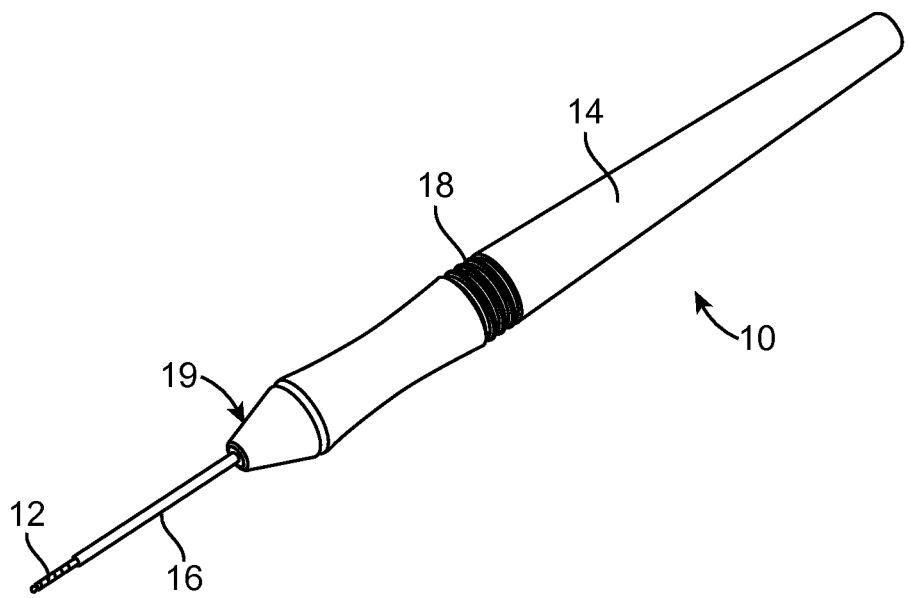
FIG. 3 shows a perspective view of an embodiment of a direct visualization (DV) system.

FIG. 3 shows a perspective view of an embodiment of a DV system 10 which can be comprised of a hand-held tool having a DV wire 12 that is movably coupled to an elongated handle 14. At least a portion of the DV wire 12 can be slidably and axially-positioned in a stopper tube 16 affixed to a distal end 19 of the handle 14. Both the stopper tube 16 and the DV wire 12 can extend outward from the distal end 19 of the handle 14. The handle 14 can be sized and shaped to be held in a single hand of a user. In addition, the handle 14 can be configured such that the DV system 10 can be operated single handedly. Furthermore, the handle 14 can have one or more gripping features 18, such as ridges and cutouts, for improved ergonomics and ease of holding.

Figure 5:
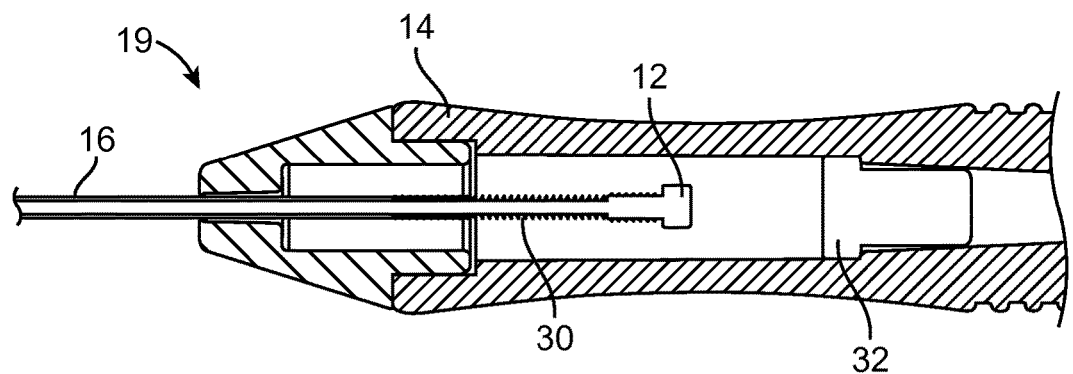
FIG. 5 shows a cross-sectional view of a portion of the DV system shown in FIG. 3.

The DV wire 12 can be coupled to a spring 30 inside the handle 14 which can allow the DV wire 12 to move inward and outward along a longitudinal axis of the DV system 10 and relative to the handle 14 and stopper tube 16. The spring 30 can provide a spring force that can assist in allowing the DV wire 12 to retract proximally into the handle 14 upon an applied force against the distal end of the DV wire 12. The spring constant of the spring 30 can be relatively low such that the DV wire 12 moves relatively easily when a force is applied. In one aspect, the spring constant can be sufficiently low such that the DV wire 12 will yield and ocular tissue is not damaged when the distal tip of the DV wire 12 is pressed against ocular tissue. In addition, a handle plug 32 (as shown in FIG. 5) inside the handle 14 can provide a hard stop for the DV wire 12 which can limit the distance that the DV wire 12 can retract into the stopper tube 16 and handle 14.

In some embodiments the stopper tube 16 can extend straight out of and along the same longitudinal axis as the handle 14. However, in some embodiments the stopper tube 16 can be curved or extend in a variety of other configurations. For example, the stopper tube 16 may be curved which can provide easier access to particular anatomical parts of the eye, such as the base of the iridocorneal angle. The distal end of the stopper tube 16 can have rounded edges which can assist in preventing damage to ocular tissue during use. In addition, the stopper tube 16 can be manufactured out of a variety of materials, such as stainless steel, titanium, plastics, or other equivalent materials, including any number of medical grade materials.

Figure 4:
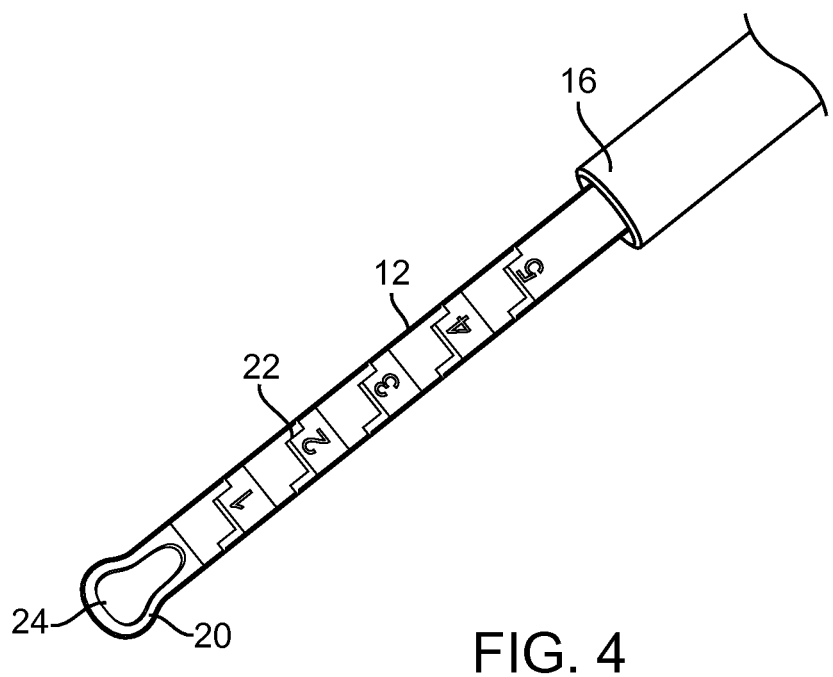
FIG. 4 shows an enlarged view of a distal end of the DV system including a part of a DV wire 12 and stopper tube 16.

FIG. 4 shows an enlarged view of the DV wire 12 and distal region of the stopper tube 16. The DV wire 12 can have a distal contact tip 20 that can be configured to be pressed against ocular tissue. The contact tip 20 may be rounded or blunt to eliminate or reduce tissue damage by the contact tip 20 when pressed against ocular tissue. In addition, one or more indicators or marks 22 can be positioned along a length of the DV wire 12. In some embodiments, one or more indicators 22 can be positioned along a length of either the DV wire 12 or stopper tube 16. The indicators 22 can assist a user in acquiring measurements of one or more anatomical features of the eye. For example, the distal end of the DV wire 12 can be placed against the base of the angle of the eye such that the user can then determine the depth of the angle.

The indicators 22 can be arranged along the DV wire 12 such that they correspond to a standard form of measurement, i.e., millimeters, fractions of an inch, etc. In such an embodiment, a user can use the DV wire 12 to make specific measurements, including measurements of particular anatomical features of the eye. In some embodiments, the indicators 22 do not correlate with a standard form of measurement and are simply reference points along the DV wire 12. In either embodiment, a user can position the DV wire 12 in the eye and use any of the indicators 22 as reference points relative to various anatomical features in the eye. As will be discussed in greater detail below, the referenced indicators 22 can assist the user in subsequent procedures, including determining an appropriately sized implant for the eye as well as assisting in correctly inserting the implant into the eye.

The DV wire 12 can be manufactured out of a variety of materials, such as stainless steel, titanium, plastics, or other equivalent materials, including any number of medical grade materials. In addition, the DV wire 12 can be at least partially tubular or hollow in order to allow one or more components, such as the measuring features discussed below, to be contained within the DV wire 12, including within the contact tip 20.

The contact tip 20 can be configured to provide sufficient surface area so as to not be traumatic to ocular tissues and/or create accidental cyclodialysis. The indicators 22 can be visible to the physician through the cornea when the DV wire 12 is extended from the stopper tube 16. In addition, the indicators 22 can be visible through the cornea so that a gonio lens is not needed in order to determine the depth of the iridocorneal angle. Furthermore, the DV system 10 can perform sufficient measurements such that a gonio lens is not necessary to perform a procedure. By relieving the need for a gonio lens to conduct a procedure, both procedure time and efficiency can be improved.

The DV wire 12 can be stamped, chemically etched, or marked with any number of patterning techniques in order to provide indicators 22 that can be seen by a user while inserted in the eye. The indicators 22 may exhibit any combination of numbering and or patterning features, with varying degrees of darkness, contrast, size, shape and color.

In some embodiments, the contact tip 20 can include a loop 24 which can provide additional damping when the contact tip 20 is in contact with ocular tissue. In addition, the contact tip 20 can be made out of a material that allows the loop 24 to deform, such as a soft or flexible material, in order to provide a damping effect. The loop 24 can be made out of the same or different material than the rest of the DV wire 12, or the loop 24 can be coated with a material, such as a flexible or soft material.

In some embodiments, deformation of the contact tip 20 or loop 24 can assist in providing a visual cue to the user that the distal end of the DV wire 12, such as the contact tip 20 or loop 24, is in contact with tissue. For example, the contact tip 20 can include one or more features having a spiral cut or any number of a variety of looped patterns which can allow for visually identifiable movements at low forces. Furthermore, deformation of the loop 24 can act as a deformable element which can provide visual cues to the user, such as when the loop 24 is in contact with tissue.

The cross section of the DV wire 12 can be rectangular, although the shape may vary. For example, the DV wire 12 can have a circular, elliptical or any one or more of a variety of cross sections along the length of the DV wire 12. In addition, the edges of the DV wire 12 can be smooth and free of sharp edges to avoid damage to tissue. The proximal end of the DV wire 12 can have ridges for holding the spring 30 in place as well as a hard stop to prevent the spring 30 from sliding off the proximal end.

FIG. 5 shows a cross-sectional view of a part of the DV system 10, including the distal end 19 of the handle 14. The DV wire 12 of the DV system 10 can be coupled to a spring 30 at a proximal region which can bias the DV wire 12 toward a distally outward direction relative to the handle 14. In addition, the spring 30 can resist movement of the DV wire 12 in a proximal direction (i.e., into the handle 14) and urge the DV wire in a distal direction (i.e., out of the handle 14).

The spring 30 can be a low force spring (i.e., a spring constant in the range of 0.001 to 0.100 Newtons). The spring 30 may be made of Nitinol, stainless steel, titanium, plastics, or other equivalent materials, and may exhibit strain induced deformation. Additionally, the spring 30 may be at least one of a tension spring, compression spring, torsion spring, leaf spring, Belleville washer, constant force spring, or urethane spring. The spring 30 may be an ultra-low force spring (i.e., less than 0.001 Newtons) for greater sensitivity, or a higher force spring (i.e., greater than 0.100 Newtons) for overcoming frictional viscous forces of aqueous fluids.

One or more features may be added or removed from the DV system 10 based on its intended use (i.e., disposable, re-usable, etc.). For example, one or more holes through the handle 14 and handle plug 32 may be included in the system in order to allow for sterilization and re-use of the DV system 10. Other features can be implemented for special or improved use of the DV system 10.

Figure 6:
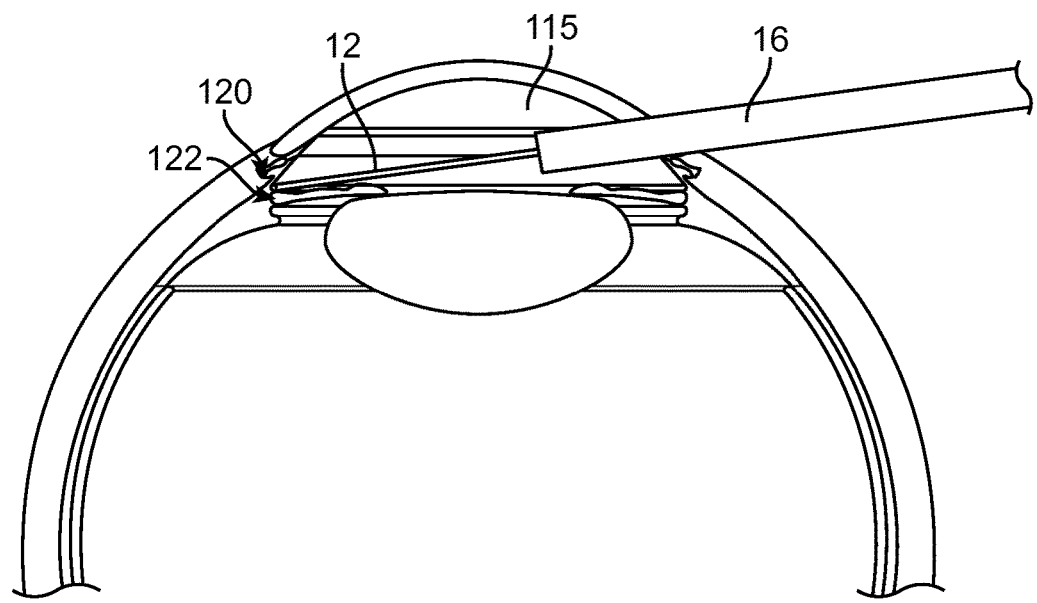
FIG. 6 shows the distal end of the DV system shown in FIG. 3 inserted into an eye.

FIG. 6 shows an example of a part of the distal region of the DV system 10 inserted in an eye. The DV system 10 can be inserted into the anterior chamber 115 of the eye via a corneal or limbal incision such that the DV wire 12 can pass across the anterior chamber 15 (pursuant to an ab-interno approach) toward the base of the angle, such as below the scleral spur 120 and above the iris 122. The distal end of the DV wire 12, such as the contact tip 20, can be pressed against ocular tissue, as shown by way of example in FIG. 6.

The DV wire 12 can apply a force against ocular tissue while the handle 14 and stopper tube 16 continue to advance in the direction of the eye. The spring 30 can allow the proximal end of the DV wire 20 to travel towards the handle plug 32 while the handle 14 and stopper tube 16 continue to travel in the direction of the eye. In some embodiments, the DV wire 20 can continue to retract into the handle 14 until the proximal end of the DV wire 20 abuts the handle plug 32. Retraction of the DV wire 20 into the stopper tube 16 and handle 14 can indicate to the user that the contact tip 20 of the DV wire 12 is properly positioned, such as the distal end of the DV wire 12 is positioned against the base of the angle. This can assist in at least minimizing damage to the ocular tissue by preventing the user from applying more force than is necessary when attempting to properly position the DV wire 12 in the eye.

Once the surgeon becomes aware that the DV wire 20 is properly positioned, the surgeon can then take appropriate measurements, such as of the iridocorneal angle of the eye. Measurements can be made by, for example, referencing the indicators 22 along the DV wire 12 relative to one or more anatomical features of the eye. After measurements have been taken, the surgeon can then retract the distal end of the DV system 10 from the eye. Any number of procedures can follow the removal of the DV system 10, including the insertion of an ocular implant.

Figure 7:
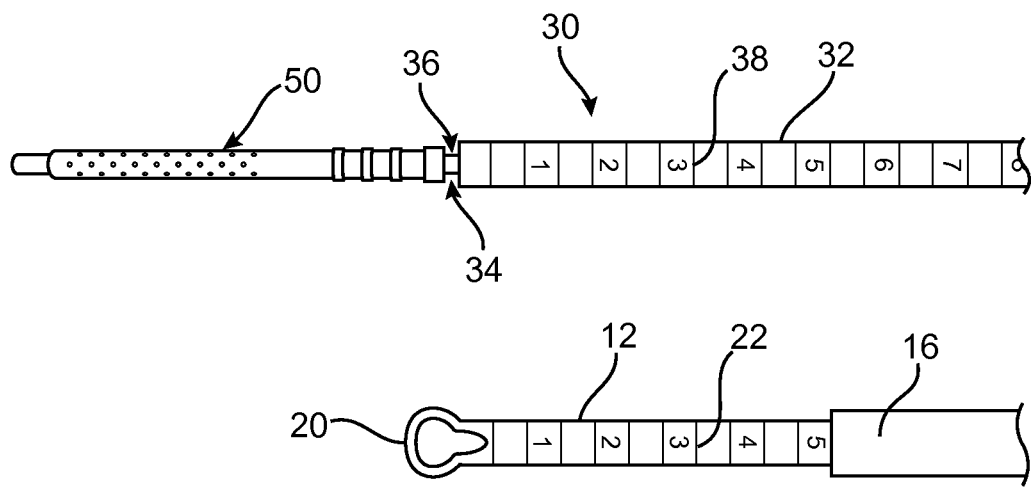
FIG. 7 shows the DV wire of the DV system aligned alongside an implant delivery applier showing the corresponding indicators.

FIG. 7 shows the distal end of the DV system 20, including the DV wire 12, aligned alongside a distal end of an implant delivery applier 30. The implant delivery applier 30 can have an elongated body 32 with an adaption feature 34 at a distal end 36 of the elongated body 32. The adaptation feature 34 can be configured to adapt one or more ocular implants 50 to the distal end 36 of the implant delivery applier 30, as shown in FIG. 7. The body 32 of the implant delivery applier 30 can include indicators or marks 38 which correspond with the indicators 22 along the DV wire 12, as also shown in FIG. 7. The corresponding indicators along the implant delivery applier 30 and DV wire 12 can allow measurements and positioning of the DV wire 12 relative to anatomical features of the eye to be easily replicated with the implant delivery applier 30, as will be discussed in greater detail below.

FIGS. 8-11 show an example method of use of the implant delivery applier 30 and DV wire 12 of the DV system 10 having corresponding marks 38 and 22, respectively, for properly inserting an implant in the eye. The method shown can be used, for example, to at least acquire one or more measurements of the eye, determine a properly sized implant and implant the properly sized implant into the eye. Furthermore, this method can be completed without the use of a gonio lens which can improve the time and efficiency of the procedure.

Figure 8:
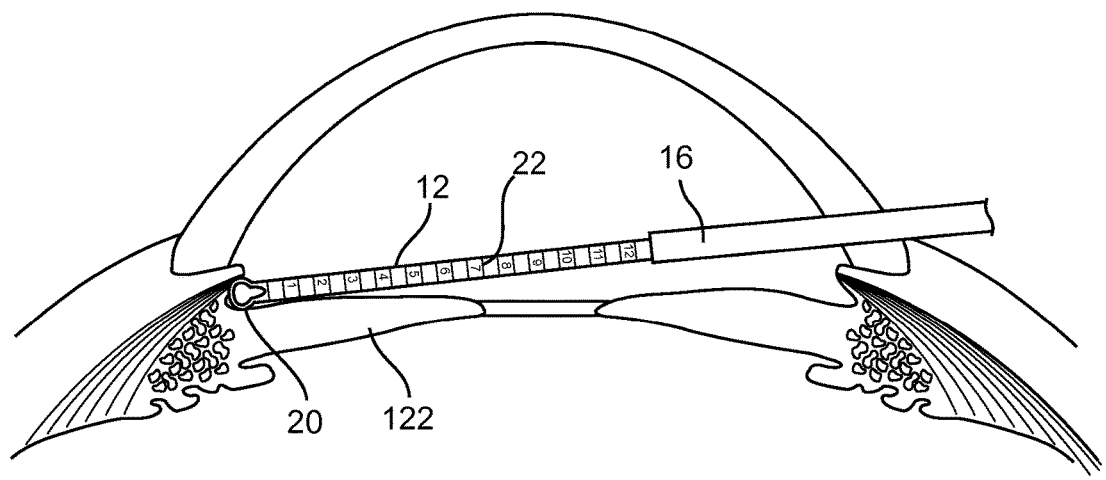
FIG. 8 shows the DV wire inserted into the eye for measuring anatomical features of the eye.

As shown in FIG. 8, a user can first insert the distal end of the DV wire 12 through a corneal or limbal incision along the eye and advance the distal end of the DV wire 12 across the anterior chamber of the eye (pursuant to an ab-interno approach). Viscoelastic substances or balanced saline solutions may be used to maintain the anterior chamber of the eye and open a space comprising a part of the angle of the eye. The incision can be approximately 0.08 mm to 2.0 mm in length and can be either created by the DV wire 12 or a separate instrument. Additionally, the incision can be approximately 1.2 mm to 1.7 mm in length.

The user can advance the DV system 10 and position the distal end of the DV wire 12 against ocular tissue, such as between the scleral spur 120 and iris 122 in order to measure the depth of the iridocorneal angle. The spring loaded feature of the DV wire 12 can assist the user in determining when the distal end, such as the loop 24 or contact tip 20, of the DV wire 12 is in contact with ocular tissue. For example, the user can continue to advance the DV system 10 into the eye until the user begins to observe the stopper tube 16 travel over the DV wire 12. Movement of the stopper tube 16 relative to the DV wire 12 can alert the user that the distal end of the DV wire 12 is positioned against ocular tissue within the eye.

Figure 9:
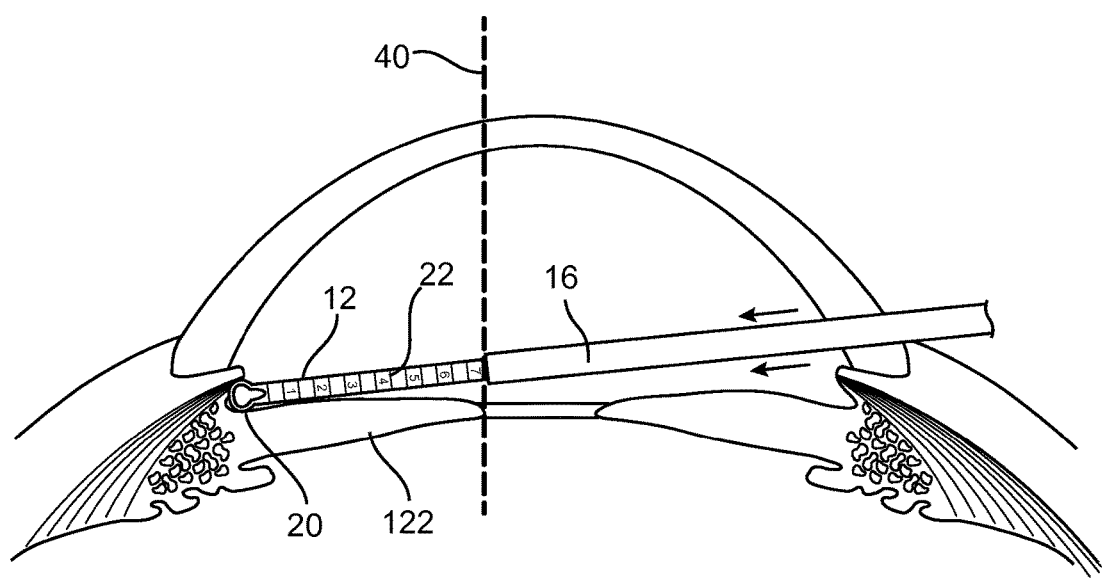
FIG. 9 shows the distal end of the DV wire abutting the base of the angle of the eye and the stopper tube in an advanced position along the DV wire.

Once the user has determined that the distal end of the DV wire 12 is positioned against the base of the angle of the eye, such as between the scleral spur 120 and iris 122, the user can take measurements of the eye using the DV wire 12. For example, the user can use the indicators 22 along the DV wire 12 to take measurements of certain anatomical features of the eye, including the depth of the angle of the eye. As shown in FIG. 9, the user can view the DV wire 12 along a generally vertical line of sight 40 in order to observe which indicator 22 is aligned with one or more anatomical features of the eye when the distal end of the DV wire 12 is positioned against the base of the angle. For example, the user can view the DV wire 12 along the vertical line of sight 40 and observe which indicator 22 is aligned with, for example, the inner edge of the iris 122. Any number of anatomical features can be measured using the indicators 22 along the DV wire 12 without departing from the scope of this disclosure.

In addition, the user can advance a feature of the DV system 10, such as the stopper tube 16, in order to assist the user in determining which indicator 22 is aligned with certain anatomical features of the eye. FIG. 9 shows an example of the stopper tube 16 being used to assist the user in determining which indicator 22 or part of the DV wire 12 aligns with the inner edge of the iris 122 when the distal end of the DV wire 12 is placed against the base of the iridocorneal angle in order to measure the depth of the angle. The stopper tube 16 can be advanced across the DV wire 12 by simply continuing to advance the DV system 10 after the distal end of the DV wire 12 is positioned against ocular tissue within the angle of the eye, as discussed above.

Once the user has obtained appropriate measurements, the user can remove the DV wire 12 from the eye. The implant 50 coupled to the implant delivery applier 30 can then be inserted into the eye. The same incision that was used to insert the DV wire 12 can be used to insert the implant delivery applier 30 and implant 50. In addition, the implant 50 can be advanced across the eye along the same or similar trajectory such that the distal end of the implant 50 contacts generally the same area of ocular tissue between the scleral spur 120 and iris 122 that the distal end of the DV wire 12 had previously contacted while taking measurements.

Figure 10:
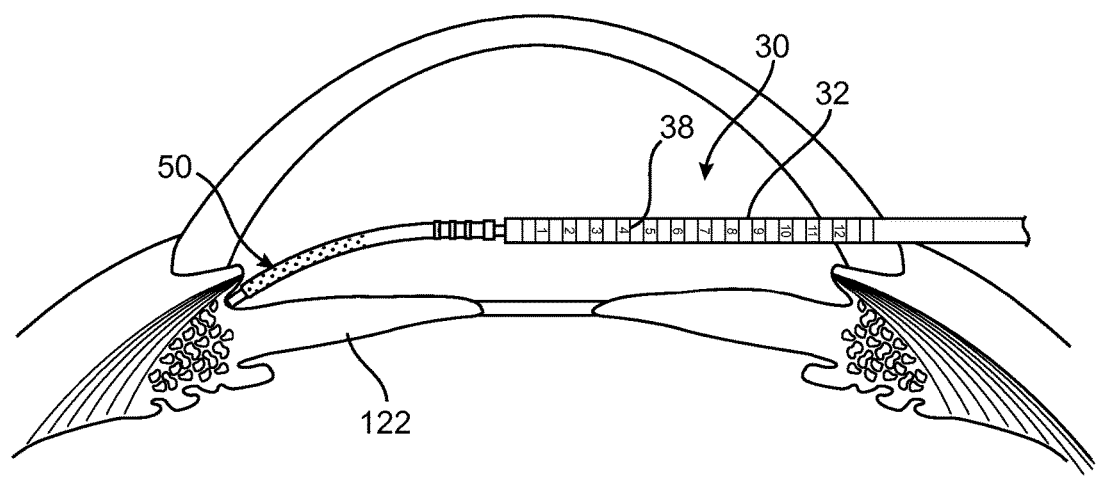
FIG. 10 shows the implant delivery applier implanting an ocular implant through the same incision the DV system used in FIGS. 8 and 9.
Figure 11:
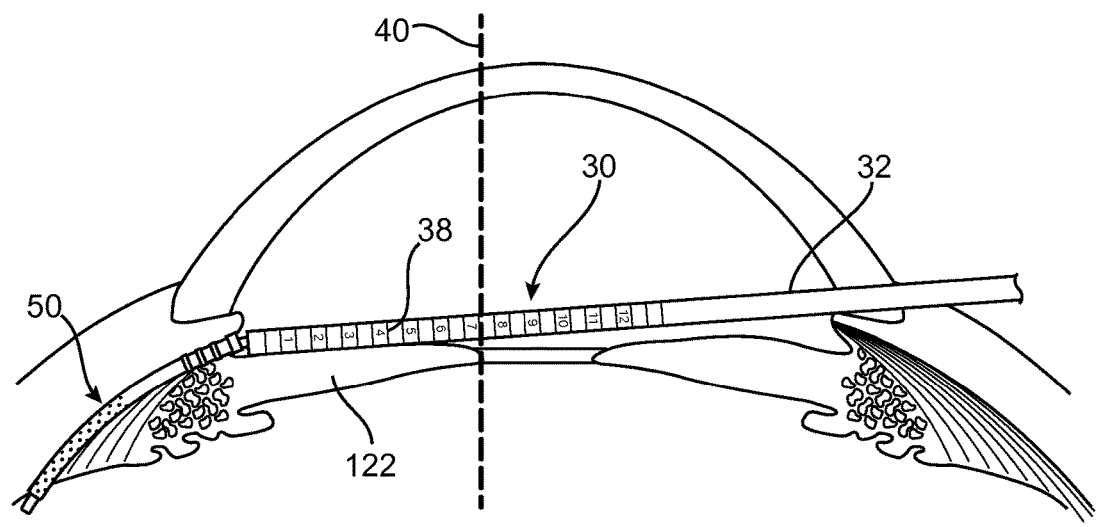
FIG. 11 shows the indicators on the implant delivery applier being used to determine the proper insertion depth of the implant.

As shown in FIGS. 10 and 11, the implant delivery applier 30 can be advanced in order to allow the implant 50 to be inserted into the suprachoroidal or supraciliary space. The user can continue to advance the implant 50 into the suprachoroidal or supraciliary space until one or more indicator 38 along the implant delivery applier 30 aligns with one or more anatomical features of the eye. In particular, the user can advance the implant delivery applier 30 until the same indicator 38 along the implant delivery applier 30 is aligned with the iris 122 as was along the DV wire 12 when the distal end of the DV wire 12 was in contact with the base of the angle (see, for example, FIGS. 9 and 11).

Figure 12:
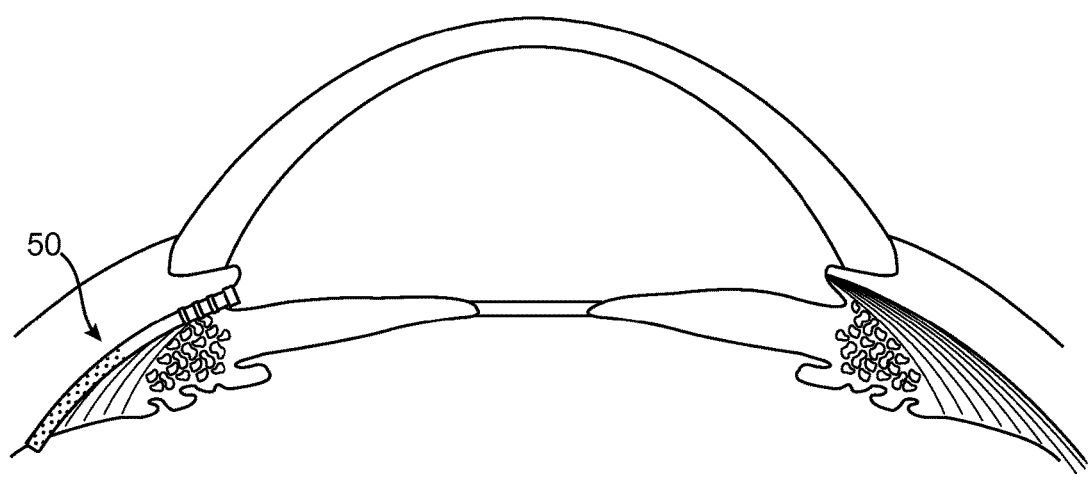
FIG. 12 shows the implant in its implanted state and providing fluid communication between the anterior chamber and the suprachoroidal or supraciliary space.

As shown in FIG. 11, the user can advance the implant delivery applier 30 until the user observes a particular anatomical feature of the eye align with an indicator 38 along the implant delivery applier 30 which corresponds to an indicator 22 along the DV wire 12 which had previously been aligned with the same particular anatomical feature, such as when the distal end of the DV wire 12 was in contact with the base of the angle. When this corresponding indicator 38 on the implant delivery applier 30 is aligned with the particular anatomical feature of the eye, the user can determine that the implant 50 is properly positioned in the eye for permanent implantation. For example, proper positioning in the eye for permanent implantation includes positioning the implant so that it can provide fluid communication between the anterior chamber and the suprachoroidal or supraciliary space without discomfort or irritation to the eye. Therefore, once the user has aligned the appropriate indicator 38 along the implant delivery applier 30 with the particular anatomical feature, the user can then release the implant 50 from the implant delivery applier 30 and remove the implant delivery applier 30 from the eye. As shown in FIG. 12, the implant 50 can then remain in the implanted position permanently or for a desired length of time.

The DV wire can be aligned with the implant delivery applier such that the distal end of the DV wire aligns with a position along the length of the head of the implant 50 when the implant 50 is coupled to the implant delivery applier 30. The alignment of the distal end of the DV wire 12 relative to the head of the implant 50 coupled to the implant delivery applier 30 can vary depending on the desired placement of the head relative to the anterior chamber of the eye when the implant 50 is in its permanently implanted position. For example, and shown by way of example in FIG. 12, it may be beneficial to have at least a portion of the head of the implant 50 extend into the anterior chamber of the eye. This can assist in ensuring that the implant 50 provides a fluid pathway between the anterior chamber and supraciliary or suprachoroidal space.

Figure 13A:
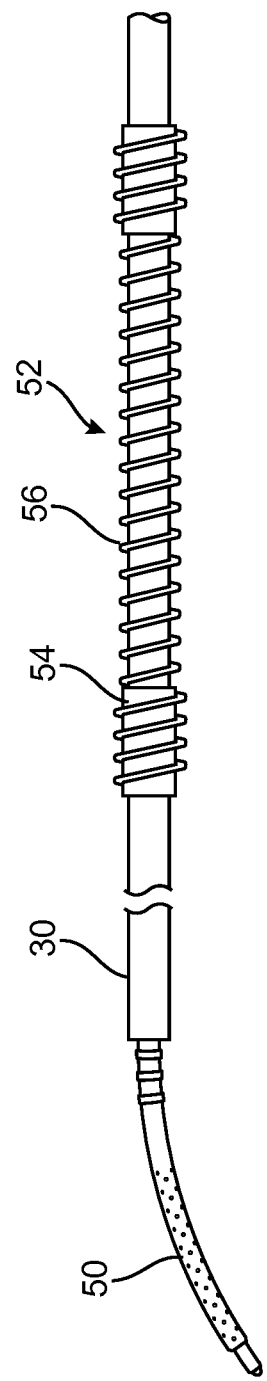
FIG. 13A shows an embodiment of the implant delivery applier having a feedback mechanism.
Figure 13B:
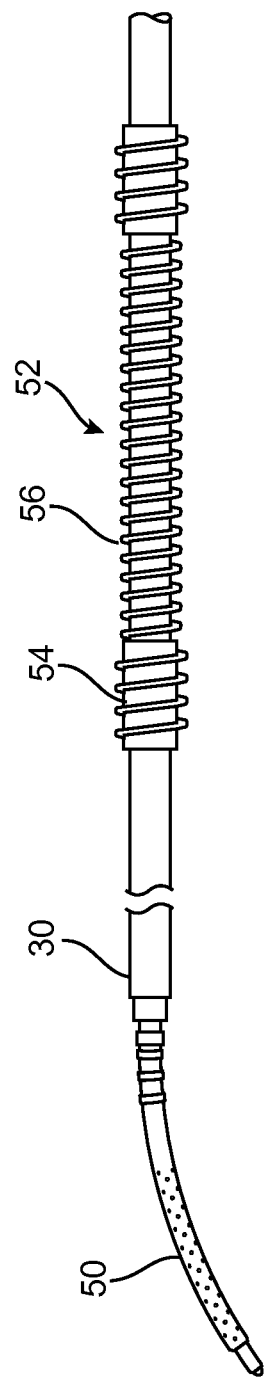
FIG. 13B shows the feedback mechanism of the implant delivery applier shown in FIG. 13A in a retracted state.

FIGS. 13A-13B shows an embodiment of a feedback mechanism 52 coupled to or comprising the implant delivery applier 30. The feedback mechanism 52 can include a sheath 54 coupled to a spring 56 at a proximal end of sheath 52. In such an embodiment, the spring loaded sheath 54 can be used to indicate depth or acknowledge when a certain landmark has been reached. For example, the sheath 54 can be positioned such that the distal end of the sheath 54 extends a distance over the implant 50 attached to the distal end of the implant delivery applier 30. Upon implantation of the implant 50 within the eye, the sheath 54 can be pushed in the proximal direction, or retracted, when the implant 54 has been implanted to a preferred depth within the eye. Retraction of the sheath 54 can indicate to a user that the sheath 54 has hit a hard stop, such as ocular tissue, and the implant 50 has been properly implanted. The implant 50 can then be released for permanent implantation once proper implant positioning has been determined.

In addition, the feedback mechanism 52 can assist the user in positioning the implant 50 such that the proximal end of the implant 50 is in direct communication with the anterior chamber of the eye in an implanted state. This can ensure that the implant 50 can provide a fluid path from the anterior chamber of the eye to another part of the eye, such as to the suprachoroidal or supraciliary space, and improve fluid flow within the eye.

Furthermore, the DV system 10 can be used for a variety of surgical procedures. For example, the DV system can be used to accurately locate and take measurements relating to a variety of anatomical structures, such as the trabecular meshwork and the Schlemm's Canal. The various measurements taken with the DV system 10 can be used for accurately positioning implants into one or more anatomical structures, including at least the trabecular meshwork and Schlemm's Canal.

Furthermore, in some embodiments, the distal end of the DV system 10, such as the distal end of the DV wire 12, can include non-contact measuring features for determining one or more of a measurement or a distance within the eye. For example, the distal end of the DV wire 12 can include one or more measuring features which can include ultrasound, infrared, optical coherence tomography, or the like. In some embodiments, the measuring features can assist in measuring the relative distance of an anatomical feature of the eye relative to a part of the DV wire 12, such as the distal end. Additionally, the DV wire 12 can include various other features which can assist in providing information to a user, such as pressure and temperature sensors.

In some embodiments, the handle can include a display which can indicate to a user one or more parameters measured by the DV system 10, such as by a measuring feature of the DV system 10. Information displayed on the display can include, for example, at least one or more of a distance measured between the distal end of the DV wire 12 and an anatomical feature, a measurement of an anatomical feature, a pressure exerted by the distal end of the DV wire 12 against tissue, pressure within the eye or temperature.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A method of measuring an eye, comprising:
    forming an incision in a cornea of the eye into an anterior chamber of the eye;
    introducing through the incision a distal end of a first device configured for measuring an anatomical feature of the eye, the first device comprising a handle with a wire extending out of a distal end of the handle and a distal end of the wire configured to be pressed against ocular tissue in the eye, the wire including a first series of symbols positioned along a length of the wire, the first device further comprising a spring coupled to a proximal end of the wire which biases the wire toward a distally outward direction relative to the handle, wherein the wire moves relative to the handle solely as a result of an applied force by the ocular tissue against the distal end of the wire, and wherein the wire extends along a longitudinal axis, and where the distal end of the wire has a transverse dimension relative to the longitudinal axis that is greater than a transverse dimension relative to the longitudinal axis at a location of the wire proximal to the distal end of the wire;
    passing the distal end of the wire through the incision and across the anterior chamber of the eye;
    positioning the distal end of the wire against the ocular tissue below a scleral spur and above an iris such that the applied force is generated between the ocular tissue and the distal end of the wire, wherein the applied force overcomes a spring force of the spring such that solely the applied force causes the wire to retract proximally into the handle; and
    measuring the anatomical feature of the eye by identifying one or more symbols of the first series of symbols along the length of the wire relative to an anatomical landmark in the eye;
    withdrawing the first device from the eye, the first device being designed for only the introducing, passing, positioning, measuring, and withdrawing steps; and inserting an ocular implant coupled to a second device through the incision, the second device comprising an implant delivery applier that includes a second series of symbols that correspond to the first series of symbols positioned along the length of the wire.

2. The method of claim 1, further comprising determining a size of the implant based on the measuring and coupling the implant to a distal end of the implant delivery applier.

3. The method of claim 2, further comprising advancing the implant across the anterior chamber of the eye and implanting the implant into the eye such that the implant forms a fluid communication between the anterior chamber of the eye and a suprachoroidal or supraciliary space.

4. The method of claim 1, wherein each of the symbols of at least one of the first series of symbols and second series of symbols is a number.

5. The method of claim 1, wherein each of the symbols of at least one of the first series of symbols and second series of symbols corresponds to a reference point.

6. The method of claim 1, wherein the transverse dimension of distal end of the wire is a loop.

7. The method of claim 6, wherein the loop is deformable.

* * * * *